US009582164B2

(12) United States Patent
Stenquist

(10) Patent No.: US 9,582,164 B2
(45) Date of Patent: Feb. 28, 2017

(54) DIALYSIS APPARATUS WITH VERSATILE USER INTERFACE AND METHOD AND COMPUTER PROGRAM THEREFOR

(71) Applicant: GAMBRO LUNDIA AB, Lund (SE)

(72) Inventor: Anita Stenquist, Sandby (SE)

(73) Assignee: Gambro Lundia AB, Lund (SE)

(*) Notice: Subject to any disclaimer, the term of this patent is extended or adjusted under 35 U.S.C. 154(b) by 231 days.

(21) Appl. No.: 14/424,769

(22) PCT Filed: Aug. 27, 2013

(86) PCT No.: PCT/EP2013/067706
§ 371 (c)(1),
(2) Date: Feb. 27, 2015

(87) PCT Pub. No.: WO2014/033119
PCT Pub. Date: Mar. 6, 2014

(65) Prior Publication Data
US 2015/0227293 A1 Aug. 13, 2015

Related U.S. Application Data

(60) Provisional application No. 61/695,546, filed on Aug. 31, 2012.

(30) Foreign Application Priority Data

Aug. 31, 2012 (SE) ........................ 1250971

(51) Int. Cl.
G06F 3/00 (2006.01)
G06F 3/0484 (2013.01)
(Continued)

(52) U.S. Cl.
CPC ....... *G06F 3/04842* (2013.01); *A61M 1/3607* (2014.02); *G06F 19/3406* (2013.01); *A61M 2205/502* (2013.01); *G06F 3/04855* (2013.01)

(58) Field of Classification Search
CPC ................................................ G06F 3/04855
(Continued)

(56) References Cited

U.S. PATENT DOCUMENTS 5,772,635 A 6/1998 Dastur et al.
5,788,851 A 8/1998 Kenley et al.
(Continued)

FOREIGN PATENT DOCUMENTS

CN 102361657 2/2012
EP 0959913 12/1999
(Continued)

Primary Examiner — William Titcomb
(74) Attorney, Agent, or Firm — K&L Gates LLP

(57) ABSTRACT

An apparatus, method and computer program for performing a plurality of operation steps of a dialysis process is disclosed. In one embodiment, a process controller controls the apparatus to perform the operation steps, monitor the dialysis process and monitor sensor inputs of sensors of the apparatus. The apparatus further includes a user interface ("UI"), comprising a display, an input device and a UI controller, wherein the UI controller enables presentation of graphical data on the display, enables user interaction with the graphical data and exchanges information with the process controller. Each of the operation steps is classified as a sequential operation step or a non-sequential operation step. The UI controller, for each of the operation steps, dynamically controls enabling and disabling of interaction with displayed corresponding operation step items based on a state of the respective operation step (i.e., completed, non-completed, selectable, non-selectable).

23 Claims, 12 Drawing Sheets

(51) Int. Cl.
*G06F 19/00* (2011.01)
*A61M 1/36* (2006.01)
*G06F 3/0485* (2013.01)

(58) Field of Classification Search
USPC .......................................................... 715/753
See application file for complete search history.

(56) References Cited

U.S. PATENT DOCUMENTS

| | | | |
|---|---|---|---|
| 5,807,336 A | 9/1998 | Russo et al. | |
| 5,885,245 A | 3/1999 | Lynch et al. | |
| 5,903,211 A | 5/1999 | Flego et al. | |
| 5,956,023 A | 9/1999 | Lyle et al. | |
| 6,353,817 B1 | 3/2002 | Jacobs | |
| 7,319,386 B2 | 1/2008 | Collins, Jr. et al. | |
| 7,904,822 B2 | 3/2011 | Monteleone | |
| 7,945,452 B2 | 5/2011 | Fathallah et al. | |
| 7,988,850 B2 * | 8/2011 | Roncadi | A61M 1/16 210/321.65 |
| 7,996,245 B2 | 8/2011 | Gejdos et al. | |
| 8,075,509 B2 | 12/2011 | Molducci et al. | |
| 8,197,432 B2 | 6/2012 | O'Mahony et al. | |
| 8,267,308 B2 * | 9/2012 | Devergne | A61M 1/16 235/375 |
| 8,529,496 B2 | 9/2013 | Britton et al. | |
| 8,956,292 B2 * | 2/2015 | Wekell | A61B 5/02055 600/301 |
| 9,101,279 B2 * | 8/2015 | Ritchey | G03B 37/00 |
| 2002/0085952 A1 | 7/2002 | Ellingboe et al. | |
| 2003/0098890 A1 | 5/2003 | Makinen | |
| 2004/0021693 A1 | 2/2004 | Monteleone | |
| 2004/0088189 A1 | 5/2004 | Veome et al. | |
| 2004/0267183 A1 * | 12/2004 | Chevallet | A61M 1/16 604/5.01 |
| 2005/0137653 A1 | 6/2005 | Friedman | |
| 2005/0209546 A1 * | 9/2005 | Jonsson | A61M 1/367 604/4.01 |
| 2006/0064020 A1 | 3/2006 | Burnes et al. | |
| 2006/0116639 A1 | 6/2006 | Russell | |
| 2006/0258985 A1 | 11/2006 | Russell | |
| 2007/0027733 A1 | 2/2007 | Bolle et al. | |
| 2007/0235376 A1 | 10/2007 | Daniel | |
| 2008/0027368 A1 | 1/2008 | Kollar et al. | |
| 2008/0033402 A1 | 2/2008 | Blomquist | |
| 2008/0033749 A1 | 2/2008 | Blomquist | |
| 2008/0176210 A1 | 7/2008 | Moll et al. | |
| 2008/0249377 A1 | 10/2008 | Molducci et al. | |
| 2008/0307353 A1 | 12/2008 | Molducci et al. | |
| 2009/0054743 A1 * | 2/2009 | Stewart | G06T 11/206 600/301 |
| 2009/0177992 A1 | 7/2009 | Rubalcaba, Jr. et al. | |
| 2010/0010428 A1 | 1/2010 | Yu et al. | |
| 2010/0030302 A1 | 2/2010 | Blowers et al. | |
| 2010/0063840 A1 | 3/2010 | Hoyme | |
| 2010/0076364 A1 | 3/2010 | O'Mahony et al. | |
| 2010/0100848 A1 | 4/2010 | Ananian et al. | |
| 2010/0121246 A1 | 5/2010 | Peters et al. | |
| 2010/0198618 A1 | 8/2010 | Oliver et al. | |
| 2010/0251114 A1 | 9/2010 | Wehba et al. | |
| 2010/0318578 A1 | 12/2010 | Treu et al. | |
| 2011/0028882 A1 | 2/2011 | Basaglia | |
| 2011/0118573 A1 | 5/2011 | McKenna | |
| 2011/0201989 A1 * | 8/2011 | Holmer | A61M 1/16 604/6.11 |
| 2011/0284464 A1 | 11/2011 | Roncadi et al. | |
| 2012/0029937 A1 | 2/2012 | Neftel | |
| 2012/0109037 A1 | 5/2012 | Ellingboe et al. | |
| 2013/0012876 A1 | 1/2013 | Debelser | |
| 2013/0015980 A1 | 1/2013 | Evans | |
| 2013/0274644 A1 * | 10/2013 | Hertz | A61M 1/16 604/6.09 |
| 2013/0298062 A1 | 11/2013 | Dolgos et al. | |
| 2013/0310726 A1 | 11/2013 | Miller et al. | |
| 2014/0115101 A1 * | 4/2014 | Wittner | G06F 19/3412 709/217 |
| 2014/0248600 A1 * | 9/2014 | Hertz | A61M 1/3643 435/2 |
| 2014/0282170 A1 | 9/2014 | Garibaldi et al. | |

FOREIGN PATENT DOCUMENTS

| | | |
|---|---|---|
| EP | 0959980 | 6/2005 |
| EP | 1917053 | 9/2010 |
| EP | 2 314 333 | 7/2012 |
| WO | 9835747 | 8/1998 |
| WO | 02/069793 | 9/2002 |
| WO | 2008074316 | 6/2008 |
| WO | 2010/027437 | 3/2010 |
| WO | 2011/144747 | 11/2011 |

* cited by examiner

DIALYSIS APPARATUS WITH VERSATILE USER INTERFACE AND METHOD AND COMPUTER PROGRAM THEREFOR

CROSS REFERENCE TO RELATED APPLICATIONS

The present application is a National Stage of International Application No. PCT/EP2013/067706, filed on Aug. 27, 2013, which claims priority to Sweden Patent Application No. 1250971-7, filed Aug. 31, 2012, and U.S. Provisional Application No. 61/695,546, filed Aug. 31, 2012, the entire contents of which are being incorporated herein by reference.

TECHNICAL FIELD

The present invention generally relates to an apparatus for performing a dialysis process, a method for such an apparatus, and a computer program for implementing the method. In particular, the invention relates to an improved user interface approach for dialysis apparatuses.

BACKGROUND

Apparatuses for dialysis process, e.g. dialysis apparatuses and possible attached apparatuses such as water cleaners, substrate supply, medical file systems, etc., normally have a user interface, UI, that is rigidly connected to the hardware of the apparatus. The user will thus need to be trained on that particular apparatus, and the apparatus will be limited in what context it can be used.

US 2008/0176210 A1 discloses a dialysis apparatus having a program library comprising several data sets, each corresponding to a functional process. The programs stored in the program library include configuration data sets, user wishes and further information items. For establishing the data sets, a computer receives a model of the dialysis apparatus which is adapted to have parameters entered, and will simulate a functional process with these parameters. Subsequent to such a functional process, the respective data set will be stored in the program library. A larger number of data sets and thus functional processes can be at disposal of an experienced user than to an average-skilled nurse. The latter kind of users will be given a restricted range of options. A specific and optimised treatment process can thus be used without entailing a risk of misguided operation by normal health-care personnel since the handling of the blood treatment apparatus is reduced to those operating steps which are absolutely required. This provides for some degree of flexibility, but still suffers from the static behaviour of the apparatus once a data set has been selected prior the treatment, and the limitation to pre-programmed data sets, which in practice will not fit optimally to each combination of treatment and user.

It is therefore a desire to provide an enhanced UI, which in turn will provide a more versatile apparatus for dialysis.

SUMMARY

An object of the invention is to at least alleviate the above stated problem. The present invention is based on the understanding that ability to provide the correct amount of information to a user will make handling more efficient to all users, irrespective if they are highly trained and need only very little information or just uses an apparatus now and then and requires a lot more information, including some guidance.

According to a first aspect, there is provided an apparatus for performing a plurality of operation steps of a dialysis process. The apparatus comprises a process controller for controlling the apparatus to perform the operation steps of the dialysis process and monitor process progress of the dialysis process and monitor sensor inputs of sensors of the apparatus; and a user interface, comprising a display, an input device and a UI controller, wherein the UI controller is connected to enable presentation of graphical data on the display, and wherein the UI controller is connected to enable user interaction with the graphical data and connected to exchange information with the process controller, wherein the exchanged information is based on the user interaction of the user interface and monitoring of process progress of the dialysis process and sensor inputs of sensors of the apparatus monitored by the process controller. Each of the operation steps are classified as one of a sequential operation step, which is dependent on completion of another operation step, and a non-sequential operation step, which is independent of completion of another operation step. The UI controller is configured to represent each of the operation steps by an operation step item which is a graphical item suitable to be presented on said display. The UI controller is further configured to dynamically, for each of the operation steps, control enabling and disabling of selection among the corresponding operation step items based on a state of respective operation step, wherein a completed state is assigned to each operation step that is completed, a non-completed state is assigned to each operation step that is non-completed, a selectable state is assigned to each operation step item of an operation step that is non-sequential and each operation step item of an operation step that is sequential but only in relation to a completed operation step, and a non-selectable state is assigned to each operation step item of an operation step that is sequential in relation to a non-completed operation step.

An advantage is that operation step items are structured to enable a UI facilitate for a user to operate the apparatus.

The process controller or UI controller may be arranged to dynamically classify the operation steps during the dialysis process to determine whether an operation step is sequential or non-sequential based on any of process progress, sensor input and input parameter settings.

An advantage is that the classification of the operation steps is kept up to date to any state of the apparatus.

The process controller or UI controller may be arranged to dynamically during the dialysis process add or remove an operation step based on any of process progress and input parameter settings.

An advantage is that the UI control is versatile in view of any actual state of the apparatus.

The process controller or UI controller may be arranged to manage the operation steps based on any of status of peripherals or consumables used by the apparatus during the dialysis process.

An advantage is that the operation steps are kept relevant to the current hardware set-up for the apparatus.

The amount of operation guidance information of an operation step item may be selectable by the operator. An advantage is that the UI of the apparatus is adapted to the operator's choice.

One or more operation step items of said operation step items assigned a selectable state recommended to be performed next may be displayed with an indicator representing the recommendation.

An advantage is that operation of the apparatus is facilitated.

Advantages of that the UI of the apparatus is adapted to the operator's choice and/or the facilitated operation improve the efficiency and/or safe operation when using the apparatus.

All operation step items representing an operation step with a process in progress by the process controller may be displayed with a status indicator representing the progress.

An advantage is that an operator is made aware of status of an operation step in progress.

At least one of the operation step items may comprise operation substep items that represent substeps of the at least one operation step by at least one of operation guidance, parameter setting and status information, and wherein the UI controller may be arranged to enable displaying of the operation substep items upon displaying of the corresponding operation step item.

An advantage is that the structured items enable a UI that further facilitates for a user to operate the apparatus.

The UI controller may be arranged to enable the displaying of the operation substep items upon displaying of the corresponding operation step item based on an input from the operator, wherein such enabling based on input from the operator overrides any corresponding disabling of the displaying of the operation substep items by the UI controller.

An advantage is that the operator is enabled to gain support from the further structured operation substep items on demand.

The UI controller may be arranged to disable the displaying of the operation substep items upon displaying of the corresponding operation step item based on an input from the operator.

An advantage is that the operator is enabled to avoid excessive, for the actual desire of the operator and for the situation, information and/or support from the UI, which may improve efficiency in operating the apparatus.

The UI controller may be arranged to disable the displaying of the operation substep items upon displaying of the corresponding operation step item based on a determined skill level of the operator.

An advantage is that the operator is enabled to automatically avoid excessive, for the actual operator and situation, information and/or support from the UI, which may improve efficiency in operating the apparatus.

At least one of the operation substep items may comprise operation substep items on a further level of detail that represent operation substeps on a further level of detail of the at least one substep by at least one of operation guidance, parameter setting and status information, and wherein the UI controller may be arranged to enable displaying of the operation substep items on a further level of detail upon displaying of the corresponding operation substep item.

An advantage is that the operator is enabled to gain support from the still further structured operation substep items on a further detail on demand.

The UI controller may be arranged to enable the displaying of the operation substep items on a further level of detail upon displaying of the corresponding operation substep item based on an input from the operator, wherein such enabling based on input from the operator overrides any corresponding disabling of the displaying of the operation substep items on a further level of detail by the controller.

The UI controller may be arranged to disable the displaying of the operation substep items on a further level of detail upon displaying of the corresponding operation substep item based on an input from the operator.

Advantages is that the UI of the apparatus is adapted to the operator's choice and/or facilitated operation, which improve the efficiency and/or safe operation when using the apparatus.

The UI controller may be arranged to disable the displaying of the operation substep items on a further level of detail upon displaying of the corresponding operation substep item based on a determined skill level of the operator.

An advantage is that the operator is enabled to automatically avoid excessive or gain necessary additional, for the actual desire of the operator and for the situation, information and/or support from the UI, which may improve efficiency in operating the apparatus.

The UI controller may be arranged to enable displaying of all of said operation step items assigned a selectable state through said UI.

An advantage is that the operator gains an improved overview of feasible operation steps to work with, which may improve the operation of the apparatus.

The UI controller may be arranged to enable displaying of only a subset of said operation step items assigned a selectable state through said UI.

An advantage is that the operator gains a focused view of for example recommended operation steps to work with, which may improve the operation of the apparatus.

An operation step may be assigned a completed state by any of user interaction through said user input device, a signal from said process controller, and a sensor signal from a sensor of the apparatus, or any combination thereof.

An advantage is that a structured record of finished operations is kept.

The UI controller may, based on said assignment, be arranged to enable one or more of said operation step items assigned a non-selectable state to be displayed through said UI.

An advantage is that an overview of operation steps may be provided to the operator. One or more operation step items of completed operation steps may be displayed with a status indicator representing the completion. All operation step items of completed operation steps on which a sequential operation step relies upon may be displayed. Alternatively, all operation step items of completed operation steps may be displayed.

Advantages of the different modes to displaying information related to the completed operations steps is that the operator is given an overview of operations performed. This may be particularly advantageous upon change of operator during the procedure.

According to a second aspect, there is provided a method of an apparatus for a dialysis process comprising a plurality of operation steps. The method comprises determining whether any of said plurality of operation steps are sequential or non-sequential, wherein a sequential operation step is an operation step that is dependent on completion of another operation step, and a non-sequential operation step is independent of completion of another operation step; representing each of the operation steps as an operation step item being a graphical item suitable to be presented on said display; assigning a completion state for each of the operation steps wherein a completed state is assigned to each operation step that is completed, a non-completed state is assigned to each operation step that is non-completed, and assigning a selectability state for each of the operation step items wherein a selectable state is assigned to each operation step item of an operation step that is non-sequential and each operation step item of an operation step that is sequential but only in relation to a completed operation step, and a non-selectable state is assigned to each operation step item of an operation step that is sequential in relation to a non-completed operation step; and enabling, based on said assignment, two or more of said operation step items of operation steps assigned a selectable state to be displayed through a UI of the apparatus, and selection among those items through an input device of the UI.

Advantages of the second aspect correspond to those of the first aspect, and advantages of embodiments of the second aspect also correspond to the corresponding embodiments of the first aspect.

The assigning of the states may comprise forming a structure of operation step items where the items are mapped to state parameters of their corresponding operation steps.

The determining whether an operation step is sequential or non-sequential may be made dynamically during the dialysis process based on any of process progress and input parameter settings.

The determining may be made dynamically during the dialysis process including adding or removing an operation step based on any of process progress and input parameter settings. The adding or removing of the operation step may be based on any of status of peripherals or consumables used by the apparatus during the dialysis process.

The method may comprise receiving an input from an operator; and selecting the amount of operation guidance information of an operation step item based on the input.

The method may comprise displaying one or more operation step items of said operation step items assigned a selectable state and recommended to be performed next are displayed with an indicator representing the recommendation.

The method may comprise displaying all operation step items representing an operation step with a process in progress by the process controller with a status indicator representing the progress.

At least one of the operation step items may comprise operation substep items that represent operation substeps of the at least one operation step by at least one of operation guidance, parameter setting and status information, and the method may comprise enabling displaying of the operation substep items upon displaying of the corresponding operation step item.

The method may comprise receiving an input from the operator; and enabling the displaying of the operation substep items upon displaying of the corresponding operation step item based on the input, wherein such enabling based on input from the operator overrides any corresponding disabling of the displaying of the operation substep items by the UI controller.

The method may comprise receiving an input from the operator; and disabling the displaying of the operation substep items upon displaying of the corresponding operation step item based on the input.

The method may comprise disabling the displaying of the operation substep items upon displaying of the corresponding operation step item based on a determined skill level of the operator.

At least one of the operation substep items may comprise operation substep items on a further level of detail that represent substeps on a further level of detail of the at least one substep by at least one of operation guidance, parameter setting and status information, and the method may comprise enabling displaying of the operation substep items on a further level of detail upon displaying of the corresponding operation substep item. The method may comprise receiving an input from the operator; and enabling the displaying of the operation substep items on a further level of detail upon displaying of the corresponding operation substep item based on the input from the operator, wherein such enabling based on input from the operator overrides any corresponding disabling of the displaying of the operation substep items on a further level of detail by the UI controller.

The method may comprise receiving an input from the operator; and disabling the displaying of the operation substep items on a further level of detail upon displaying of the corresponding operation substep item based on the input.

The method may comprise disabling the displaying of the operation substep items on a further level of detail upon displaying of the corresponding operation substep item based on a determined skill level of the operator.

The method may comprise displaying all of said operation step items assigned a selectable state through said UI.

The method may comprise displaying only a subset of said operation step items assigned a selectable state through said UI.

The method may comprise assigning an operation step a completed state by any of a user interaction through a user input device of the apparatus, a signal from a process controller of the apparatus, and a sensor signal from a sensor of the apparatus.

The method may comprise displaying one or more of said operation step items assigned a non-selectable state through said UI.

The method may comprise displaying one or more operation step items of completed operation steps with a status indicator representing the completion. The method may comprise displaying all operation step items of completed operation steps on which a sequential operation step relies upon. Alternatively, the method may comprise displaying all operation step items of the completed operation steps.

According to a third aspect, there is provided a computer program comprising computer-executable program code which when executed by a processor of an apparatus for a dialysis process causes the apparatus to perform the method according to the second aspect.

Advantages of the third aspect, which essentially relies on the demonstrated features of the second aspect, inherently correspond to those of the second aspect, and as demonstrated above the correspond to the advantages of the first aspect, and advantages of embodiments of the third aspect also correspond to the corresponding embodiments of the first aspect.

Other objectives, features and advantages of the present invention will appear from the following detailed disclosure, from the attached dependent claims as well as from the drawings. Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of said element, device, component, means, step, etc., unless explicitly stated otherwise. The steps of any method disclosed herein do not have to be performed in the exact order disclosed, unless explicitly stated. Furthermore, as will be understood by a reader skilled within the field of technology, the multitude of features demonstrated by the disclosed examples of apparatuses, methods and computer programs, may be combined or configured to be used together with other of those features although not explicitly demonstrated as a particular example. The skilled reader will also recognise the relations between the apparatus, method and computer program examples and is encouraged to contemplate the principles of the features irrespective of whether the given example is an apparatus, method or computer program.

BRIEF DESCRIPTION OF THE DRAWINGS

The above, as well as additional objects, features and advantages of the present invention, will be better understood through the following illustrative and non-limiting detailed description of embodiments of the present invention, with reference to the appended drawings.

DETAILED DESCRIPTION

Figure 1:
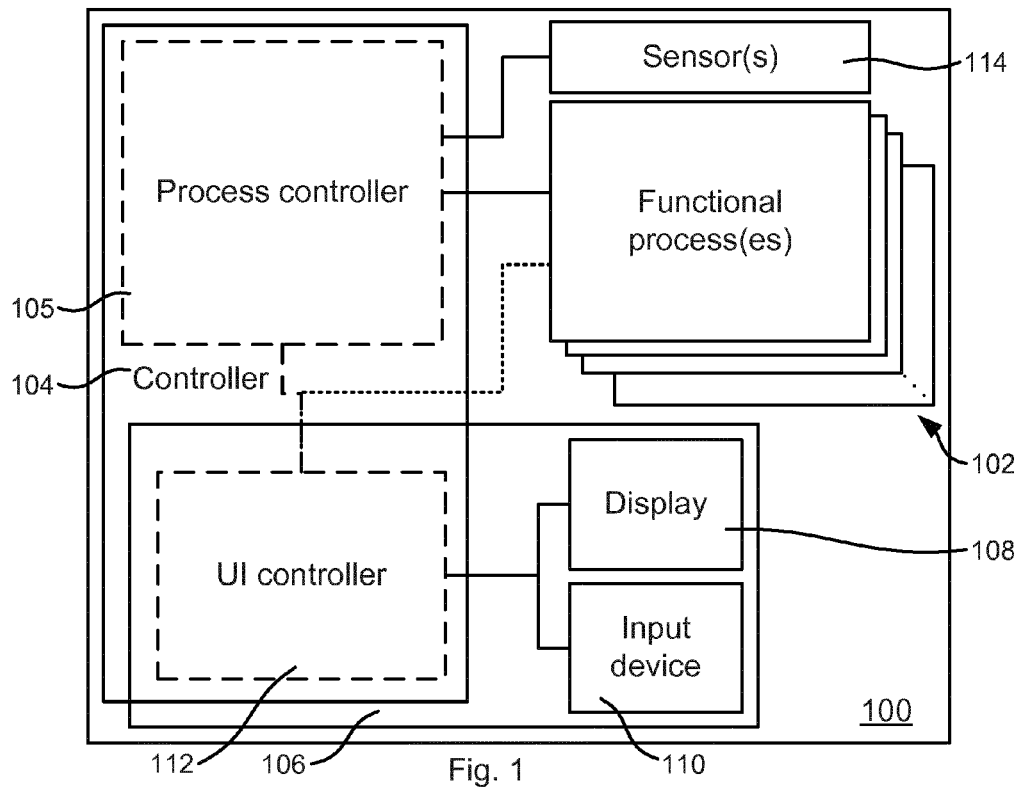
FIG. 1 is a block diagram schematically illustrating an apparatus for a dialysis process.

FIG. 1 is a block diagram schematically illustrating an apparatus 100 for a dialysis process. The dialysis process is performed by one or more functional processes 102, which may be separate units within the apparatus 100, functionally separate tasks performed by same unit within the apparatus 100, or two or more units within the apparatus 100 jointly performing a functional process. Such a functional process 102 may be water treatment for the dialysis, rinsing mechanism, extracorporeal blood circuit mechanism, etc. A controller 104 of the apparatus controls the operation of the functional processes; thus, the process controller 104 may be a joint controller, a multitude of local controllers, or a hierarchy of controllers working together. The controller 104 may comprise a process controller 105 which may be a separate controller, but may as well be a functional part of the controller structure of the apparatus 100 as a whole. The controller 104 or process controller 105, depending on the configuration, monitors inputs from one or more sensors 114 of the apparatus, such as pressure, temperature, air or (mechanical) position sensors, etc. After this brief description of feasible structures of an apparatus for dialysis, it is already possible to understand that a user, i.e. an operator, such as a nurse, technician or other care personnel, or patient, e.g. at home treatment, is not capable of knowing all the details of different units and/or functional processes of the apparatus 100. Instead, a user interface, UI, 106 is provided, and the aim is to make the UI 106 as convenient to use for the user as possible. The UI 106 comprises an output device such as a display 108 and an input device 110 to be able to interact with the user. The display 108 and the input device 110 may be integrated to a touchscreen. Also other input and output devices may be present such as speaker, signal light indicator, tactile actuator, etc. for output and keyboard or keypad, knob, button, switch, microphone, trackball, touchpad, joystick, mouse, stylo, etc. for input. The UI 106 may comprise a UI controller 112 which controls the features of the UI, as will be further demonstrated below. The UI controller 112 may be a separate controller, but may as well be a functional part of the controller structure of the apparatus 100 as a whole, i.e. of the controller 104.

The UI 106 is connected to the process controller 104 for interchanging of signals, both for providing control data to process controller 104 such that it is able to control the functional processes 102 to make the apparatus 100 perform the desired tasks of the user, and for receiving status and measured data from the controller 104 to be able to adapt behaviour of the UI 106 and/or present relevant data to the user The UI 106 may also be connected directly to sensors 114 of the apparatus 100, e.g. associated with the functional processes, for the same reasons.

The functional processes 102 and their related units are each arranged to perform their tasks. Simultaneously, the user defines the tasks for the apparatus in maybe a different way. There is therefore a desire to bridge any such differences between the user's viewpoint and the machine's structure. The user's intentions with the treatment by the apparatus are thus not only transferred via the UI to the functional processes, but also in some sense translated. Similar applies for data going the other way. Roughly, the user's intentions (and need for information) are here mapped on operation step items which may be presented and/or interacted with through the UI, wherein the operation step items are related to corresponding operation steps, which in turn are actions (and information collection) performed by the functional processes of the apparatus.

A further consideration is the diversity of users, as given by the examples above. What is as convenient as possible to use for one user may not be that for another. Therefore, there is also an aim to provide flexibility of the UI. However, since dialysis is serious matter for the patient, and security in treatment is highest priority, there are several considerations to be made upon providing a flexible UI.

The operation steps may be of different nature. As discussed above, each operation step is configured to provide, through its operation step item, an understandable function for the user. If the operation step is not understandable enough for some users, the operation step may be divided into substeps, which in turn may be divided into further levels of detail. The operation steps may also depend on each other, such that one operation step cannot be performed until another operation step is completed. Similar characteristics may apply to the substeps and the further detailed steps. Such a step is here referred to a sequential step since it needs to be done in sequence after another step that has been completed. Thus, non-sequential steps may be done anytime, at least in sense of the state of other steps. Consequently, the nature of a sequential step changes when the step on which it relies on becomes completed. Under some circumstances, a non-sequential step may also become a sequential step. This may for example be when operation steps are added, e.g. depending on change of the apparatus set-up. Removal of operation steps is also possible due to change of apparatus set-up, parameter settings, selected treatment type, etc. These dynamic features calls for the UI controller 106 to be arranged to dynamically determine whether any of a plurality of operation steps of a dialysis process are sequential or non-sequential, and if sequential operation steps relies on any non-completed operation step. The determination may be a continuously running process, which may be advantageous since the properties changes all the time, e.g. depending on progress of the dialysis process, change of parameter settings, etc. The operation steps are represented by the operation step items, which may include user understandable information or references to such information, such as operation guidance, parameter setting, status information, etc. From these items, the UI controller 106 may form a structure, e.g. a formal data structure, a state machine, or real-time state structure, of the assignments which form basis for the control of the UI. In the structure, the operation step items are assigned as selectable if their operation steps are non-sequential or sequential but only in relation to a completed operation step. That is, a selectable operation step item is that because it is available for being performed and is not waiting for another operation step to be completed. Thus, non-selectable operation step items are such since they are not available for being performed. Regarding the completed steps, these are mostly not available, but some may be, e.g. for changing a parameter that already has a value, i.e. may be regarded as completed. On the other hand, a similar completed step with a set parameter may not be available since the parameter needs to be kept constant for other operation steps being in progress. In which case, the information that an operation step is completed is of benefit for the formed structure.

The versatility of the UI is provided since the UI controller is arranged to enable two or more selectable operation step items to be displayed through the UI and enable a user to interact with the displayed operation step items. The user may thus select any of the presented operation step items to start working with since the structure has sorted out the selectable operation step items are possible to work with.

The UI may of course also display non-selectable operation step items for information, but preferably with some distinction in appearance between the selectable and non-selectable. Also completed operation step items may be displayed, for information if non-selectable and for operation if selectable, preferably with an indication that the operation step items relate to operation steps that are completed.

The amount of displayed UI items may be selected to provide relevant information to the user, while excess information that may confuse the user or obscure the relevant information may be avoided to be displayed.

Figure 2:
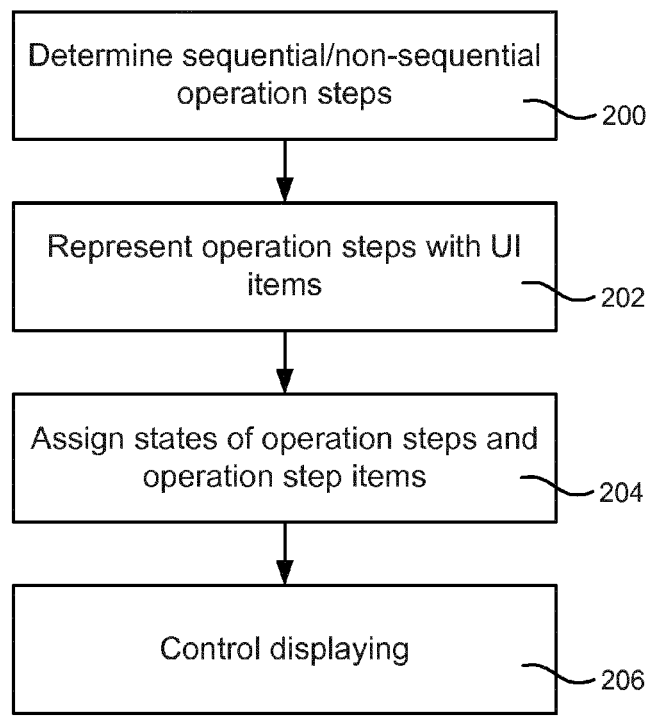
FIG. 2 is a flow chart schematically illustrating a method of an apparatus for dialysis.

FIG. 2 is a flow chart schematically illustrating a method of an apparatus for dialysis. It is determined 200 whether any of said plurality of operation steps are sequential or non-sequential. As stated above, a sequential operation step is an operation step that is dependent on completion of another operation step. Further, each of the operation steps are represented 202 by at least one of operation guidance, parameter setting and status information as an operation step item suitable to be presented on said display. An assignment of states of operation steps and of operation step items is performed 204 where items of operation steps which are non-sequential or sequential but only in relation to a completed operation step are assigned a selectable state, items of operation steps which are sequential in relation to a non-completed operation step are assigned a non-selectable state, and items of operation steps which are completed are assigned a completed state. The assignment 204 may include forming a data structure for handling the assignments. Based on said assignment, two or more of said operation step items assigned a selectable state are enabled to be displayed 206 through a UI of the apparatus. Thereby, interaction with those items through an input device of the UI is also enabled. The dynamic properties of the approach calls for the method to be performed on a real-time basis, and the actions 200-206 should not be construed to be stepwise performed as of the boxes of the flow chart of FIG. 2. The real-time properties of the approach will be illustrated with reference to FIGS. 3 to 6. With reference to these Figs, details and options for the actions will also be demonstrated.

Figure 3:
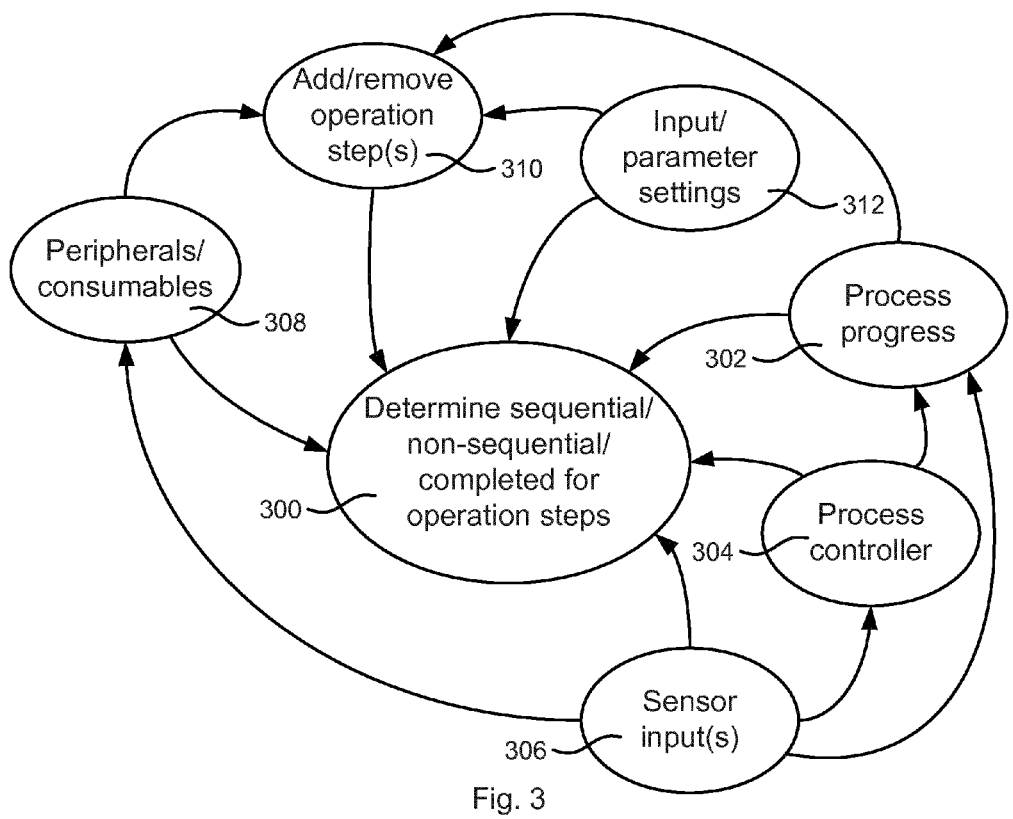
FIG. 3 is an object diagram schematically illustrating determination of properties for operation steps for initiating and performing a dialysis process.

FIG. 3 is an object diagram schematically illustrating determination of properties for operation steps for initiating and performing a dialysis process. The action corresponds to the determination action 200 of FIG. 2.

For each operation step, functional relations to one or more of states of any device, controller, sensor, inputs and parameters, process progress, and presence or state of peripheral devices or consumables are determined. Also, it is considered whether any operation step is to be removed or added. These phenomena may be modelled as objects where each object interchanges information with a determination object 300. The objects may also interchange information between the objects where such functional relationship exists. There may be a process progress object 302 which may be state monitoring interface to the process controller as demonstrated above. Information about state of the process is provided to the determination object 300 from the process progress object 302. There may also be a process controller object 304 which interchanges information with the determination object 300, e.g. about present functional processes. Here, the process controller object 304 may also interact with the process progress object 302. One or more sensor objects 306 may interact with the determination object 300, and may also interact with the process controller object 304 and/or the process progress object 302. The sensor object 306 may also interact with one or more peripherals/consumables object 308, which in turn may interact with the determination object 300, and also with an object 308 for handling addition or removal of operation steps of the dialysis process. Although not depicted in FIG. 3 for reasons of a clear and readable picture, the operation step handling object 310 may interact with any of the other objects, and may also be a part of the determination object 300. One or more objects 312 may handle inputs and/or parameter settings. The inputs and parameter settings may be provided from a user, i.e. operator or patient, or from a memory device, e.g. a patient database, a portable memory card, or a remote information provider (server). The determination object 300 thus collects data when being available from the different other objects, and may based on those data and basic properties of respective operation step determine if an operation step is sequential or non-sequential, and if an operation step is completed or non-completed. The determination object may further collect data such that it may be determined if a sequential operation step relies on a completed or non-completed other operation step, as will be further demonstrated below.

An example of an operation step may be called "Connect concentrates", which includes properly connecting a concentrate unit to the dialysis apparatus, where for example a peripherals/consumables object 308 provides information whether a concentrate unit is connected, wherein a sensor input provided through sensor input object 306 may be provided either via the peripherals/consumable object 308 or directly to the determination object. Proper connection may also be provided from sensor object 306 to the process controller object or the process progress object 302 and then on to the determination object 300. When the concentrate unit is properly connected, this operation step may be determined to be completed based on the information received from the above mentioned objects 302, 304, 306 and/or 308, but may also require a confirmation from a user via input/parameter settings object 312 for being set as completed. Inherent in the operation step properties may also be that the operation step "Connect concentrates" is non-sequential. As an alternative, this operation step may be non-sequential only if the process progress object 302 indicates the state that dialysis process is not in a treatment phase, while this operation step is sequential if the dialysis process is in a treatment phase and cannot be performed if not certain other operation steps are completed, e.g. the procedure is in a suitable state for replacing the concentrate unit (e.g. an operation step including applying certain clamps, etc.).

Figure 4:
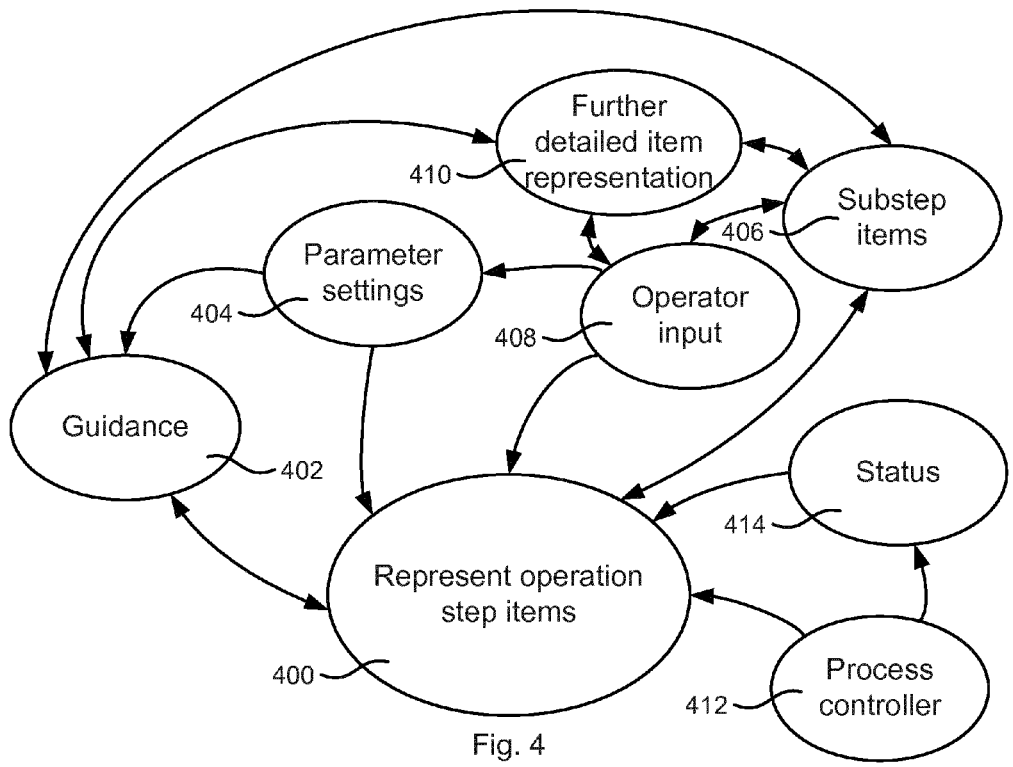
FIG. 4 is an object diagram schematically illustrating assigning representations of operation steps to operation step items suitable for user interface control.

FIG. 4 is an object diagram schematically illustrating assigning representations of operation steps to operation step items suitable for user interface control. The action corresponds to the representing action 202 of FIG. 2.

A representing object 400 is arranged to collect information that may be enabled for user interaction with each operation step and represents that as an operation step item for the respective operation step. The representing object may interact with a guidance object 402 which provides guidance information for the operation step item. The guidance may comprise several levels of detail which may be provided based on information provided from other objects, such as a parameter setting object 404 which may hold a parameter setting indicating the skill and/or training level of the user, e.g. patient, nurse, technician, etc. The level may also be chosen to be more detailed than indicated by such parameters, e.g. upon user request. This may be handled by a substep item object 406 which may call upon a more detailed guidance as a dynamic setting, e.g. upon interaction from an operator input object 408. This substep item object 406 may also interact with an object 410 for further detailed item representation, i.e. some kind of information zoom function. The object 410 may also be a part of the substep item object 406. The object 410 may also interact with the operator input object 408.

The operator input object 408 may interact with the representation object 400, and through this interact with the other objects as well.

Input of the dialysis process and other status may be provided from a process controller object 412 and/or a status tracking object 414 for populating the information of the respective operation step items.

Continuing the example of "Connect concentrates" operation step mentioned above, the operation step item may include a basic guidance by the guidance object 402 where the basic guidance includes an indication that the concentrates unit is to be attached and an indication on the type of concentrates unit to use. The substep item object 406 may provide substeps items, e.g. "Open door X", "Apply unit", "Close door and confirm action", and the further detailed item object may provide further details on how to apply the unit, e.g. "Turn lever marked A", "Insert unit with text towards you", "Turn back lever marked A". The instructions may be enhanced with images, animations, indicator lights on where to attach unit, etc. The guidance object 402 will be involved in such additional instructions. However, here it should be noted that the representation object does not display anything; it just populates the operation step items with proper information and/or pointers such that it may be used when called upon (by a display control object which will be further described with reference to FIG. 6).

Figure 5:
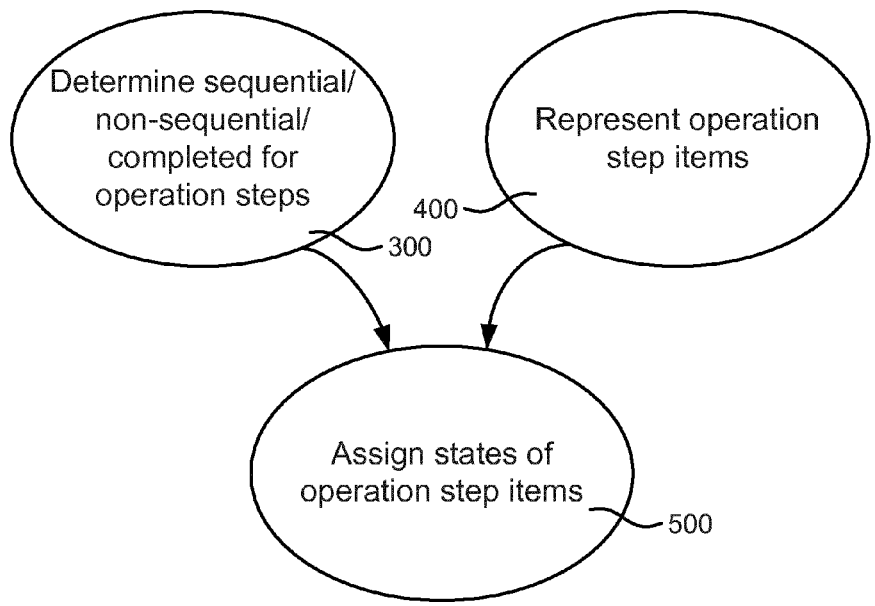
FIG. 5 is an object diagram schematically illustrating assignment of states, preferably forming a structure, preferably data structure, of operation step items.

FIG. 5 is an object diagram schematically illustrating assignment of states, preferably forming a structure, preferably data structure, of operation step items, according to an embodiment. The action corresponds to the assignment action 204 of FIG. 2.

The determination object 300 and the representation object 400 respectively provides their collected information about operation steps, i.e. by determination object 300 on properties of respective operation step in view of their functions in the apparatus and in view of the dialysis process, and about operation step items, i.e. by representation object 400 on information to be enabled to be provided to a user, such that a structure forming object 500 may form a data structure for enhancing the UI operation.

The structure may be formed by aggregating the information about the operation steps and the operation step items such that items of operation steps which are non-sequential or sequential but only in relation to a completed step are assigned a selectable state, items of operation steps which are sequential in relation to a non-completed operation step are assigned a non-selectable state. Items of operation steps which are completed are assigned a completed state, and items of operation steps which are not completed yet are assigned a non-completed state. Here, non-completed items which are in progress of being completed, but where e.g. physical properties make them unable to instantly be ready, such as heating, cooling, filling, etc. may also be assigned a degree of progress towards completion.

Figure 6:
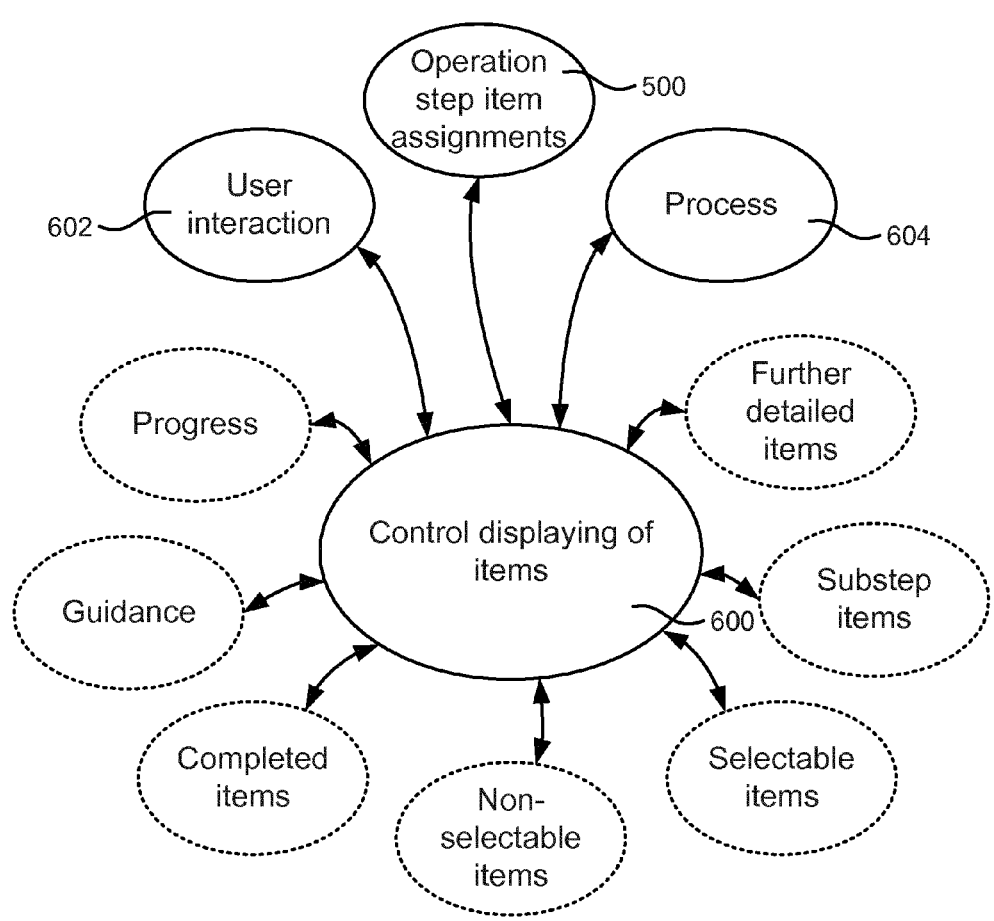
FIG. 6 is an object diagram schematically illustrating controlling of displaying operation step items through the user interface.

FIG. 6 is an object diagram schematically illustrating controlling of displaying operation step items through the user interface. The action corresponds to the display controlling action 206 of FIG. 2.

A display control object 600 provides control of what is to be displayed through the UI. For providing the desired flexibility for a user to work with the apparatus for dialysis, the control object is arranged to enable two or more of said operation step items assigned a selectable state to be displayed through said UI and enable interaction with those items through the input device. The display control object 600 gains the knowledge of which operation step items that are selectable and their possible content from the assignment, e.g. structure, object 500. The display control object 600 then selects what information to provide through the UI. This selection may be provided through an information collection from a user interaction object 602 and/or a process object 604, i.e. from man and/or from machine.

The hashed elements in the illustration are thus not real-time objects in the same sense as illustrated in the object diagrams herein, but are illustrations on information items to be enabled to be displayed for each of the operation step items, and are thus information extracted or selected from the assignment provided by the assignment object 500, e.g. a data structure.

Figure 7:
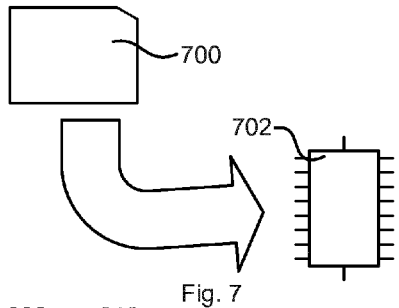
FIG. 7 schematically illustrates a computer-readable medium for storing a computer program, and a processor for executing instructions of the computer program.

FIG. 7 schematically illustrates a computer-readable medium 700 for storing a computer program, and a processor 702 for executing instructions of the computer program.

The methods according to the present invention are suitable for implementation with aid of processing means, such as computers and/or processors. Therefore, there is provided computer programs, comprising instructions arranged to cause the processing means, processor, or computer of the apparatus for dialysis, e.g. its process controller and/or UI controller to perform the steps of any of the methods according to any of the embodiments described with reference to FIGS. 2 to 6. The computer programs preferably comprises program code which is stored on a computer readable medium 700, as illustrated in FIG. 7, which may be loaded and executed by a processing means, processor, or computer 702 to cause it to perform the methods, respectively, according to embodiments of the present invention, preferably as any of the embodiments described with reference to FIGS. 2 to 6. The computer 702 and computer program product 700 may be arranged to execute the program code sequentially where actions of the any of the methods are performed stepwise. The processing means, processor, or computer 702 is preferably what normally is referred to as an embedded system. Thus, the depicted computer readable medium 700 and computer 702 in FIG. 7 should be construed to be for illustrative purposes only to provide understanding of the principle, and not to be construed as any direct illustration of the elements.

FIGS. 8 to 25 illustrate examples of displayed information according to various embodiments. The illustrations may also be considered as two examples provided according to an embodiment where different settings for the amount of information to be provided are applied to the one and same UI. Thus, FIGS. 8 to 21 illustrate a user interface example according to a first user interface setting, and FIGS. 22 to 25 illustrate a user interface example according to a second user interface setting. The first user interface setting may be considered suitable for less trained operators since it provides detailed guidance, while the second user interface setting may be considered suitable for more trained operators and provides less interaction with the user interface which may make work more efficient for the more trained operator.

Figure 8:
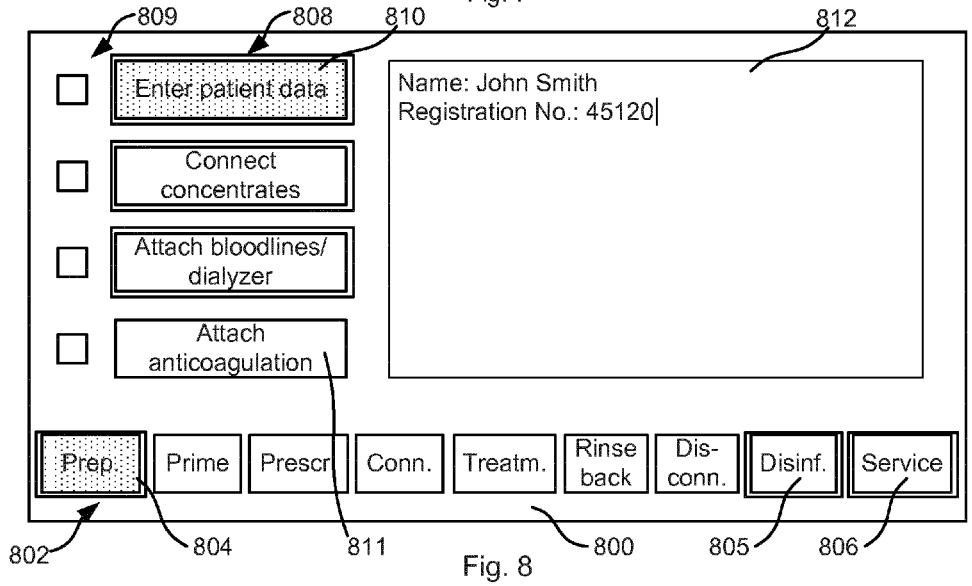
FIGS. 8 to 21 illustrate a user interface example according to a first user interface setting.

FIG. 8 illustrates a snap shot of a display screen 800 of a UI according to an embodiment. The UI in this example has a touch screen, i.e. the visual output device and the input device are integrated and aligned such that interaction may made directly on the displayed items for such items that are assigned for interaction. In the display, a number of operation step items 802 are displayed, among which some operation step items 804, 805, 806 are selectable which is indicated in some way, e.g. by an additional frame or shadowing around the respective item. Colour schemes may also be used for the indication.

In the snap shot of the display screen 800, a user has interacted with operation step item 804, which is then indicated as active, i.e. that interaction on the operation step item is ongoing, by for example the displayed operation step item 804 being dotted (also here, a colour scheme may be used). The interaction has called upon displaying of a number of subitems 808 which are displayed, and corresponding check boxes and/or status indicators 809 may also be displayed. Such check box and/or status indicators may also be provided for any of the operation step items 802. As an alternative, or additionally, an indication in the operation step item may be provided, as will be illustrated with reference to FIG. 11 where a completed item is illustrated with hatching. Other patterns and/or colour schemes may also be used for the illustration.

In the snap shot of the display screen 800, a user has interacted with operation substep item 810, which then is indicated as active, i.e. that interaction on the operation step item is ongoing, by for example the displayed operation step item 804 being dotted (also here, a colour scheme may be used). The interaction has called upon entering information associated with the operation substep item 810 which is enabled to be entered in a work area 812 of the display screen 800. This guided interaction field area 812 may be used for such input, e.g. with aid of a keyboard, keypad or the like, but may also be used for guidance information, displaying of settings or parameters, sensor values, progress information, etc. A corresponding indicator 809 may indicate completion upon the completed input. A signal on the completed input may be generated upon the operator actuating an enter/OK (soft) button.

In the snap shot of the display screen 800 it may also be seen that operation substep item 811 is not indicated as active. This is an indication to the user that this operation substep item 811 is not ready for being performed, and the processor has determined this operation substep item 811 as being sequential in relation to a non-completed operation step or operation substep.

Figure 9:
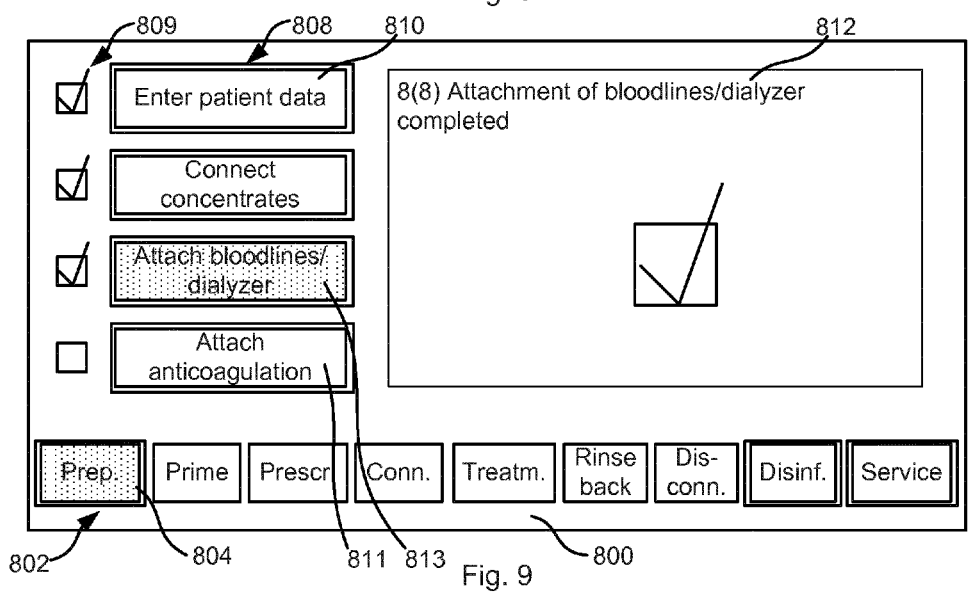

FIG. 9 illustrates a snap shot of the display screen 800 of the UI at a later time instant than that for FIG. 8, and here some of the operation substeps of items 808 are completed, which is indicated by the indicators 809. Operation substep item 813 is indicated as selected, and the guided interaction field 812 displays an operation substep item on a further level of detail related to the operation substep item 813. The operation substep on the further level of detail is illustrated to be 8 of 8 and indicates that attachment of bloodlines and/or dialyzer is completed. Thus, the former non-illustrated seven substeps on the further level of detail preferably have guided the user, step-by-step, to make the attachment. This allows for the less trained user to make the attachment correct (or for the trained user to feel more safe). As discussed above, the trained user who knows the attachment steps well, the substeps on the further level of detail need not be displayed, and the trained user may just go on with the actions This will be further discussed with reference to FIGS. 21 to 25. Here, the operation substep item 811 has become selectable, and is indicated as selectable with a frame. The processor has been able to determine this selectable condition since operation substeps on which the operation substep of operation substep item 811 depends have been completed.

Figure 10:
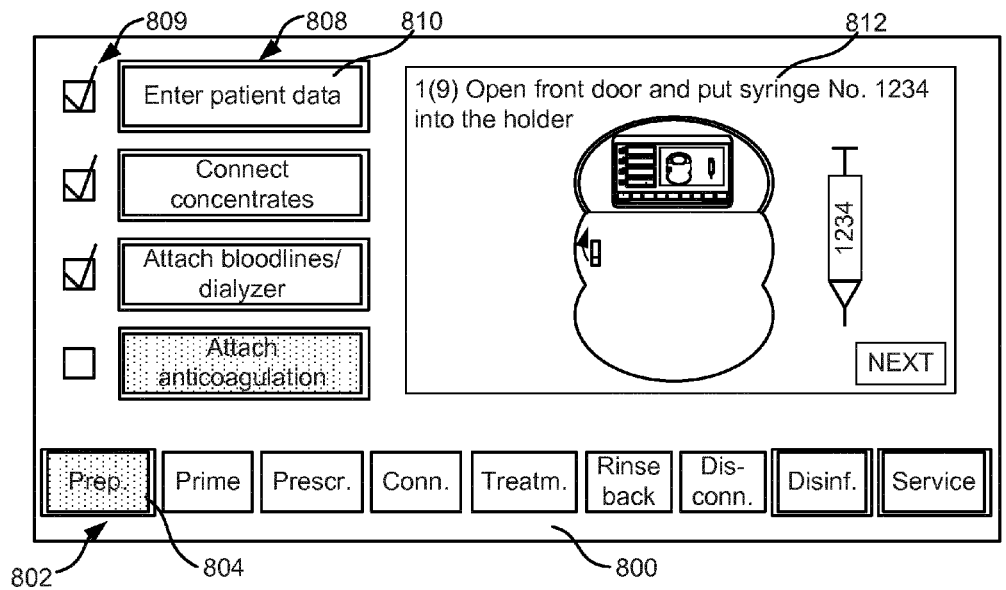
Figure 11:
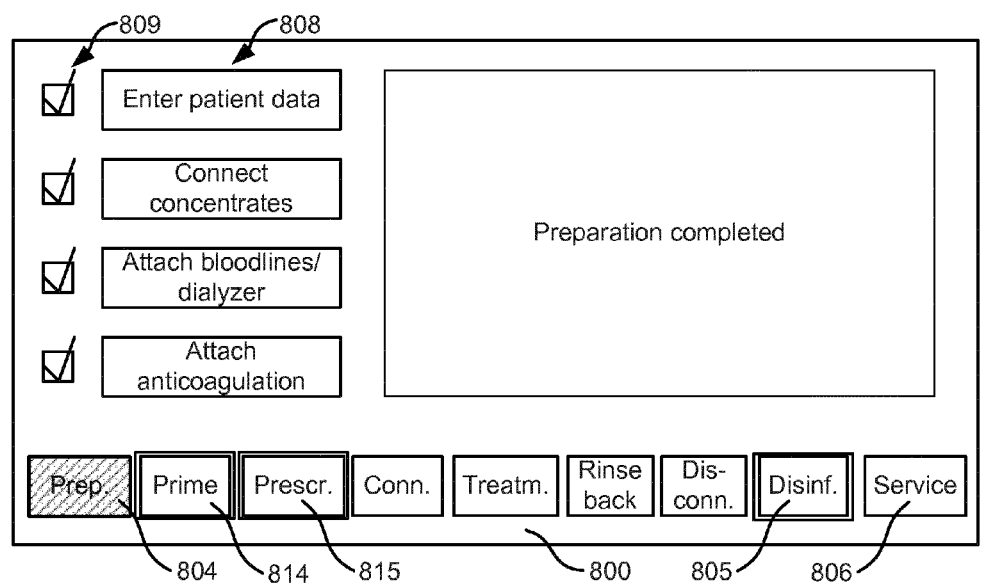

FIG. 10 is a further snap shot where the user has selected operation substep 811, and a first of nine operation substep items on a further level of detail related to the operation substep item 811 is displayed in the guided interaction field 812. Here, guidance is provided to the user. The user may press the "NEXT" soft key to proceed to the next operation substep item on a further level of detail, and/or the processor may jump to the next operation substep item on a further level of detail when sensors of the apparatus indicates that the illustrated action has been performed. FIG. 11 illustrates a snap shot of the display screen 800 of the UI at a later time instant than that for FIGS. 8 to 10, and here all the operation substeps of items 808 are completed, which is indicated by the indicators 809. Since these operation substeps are completed, and thereby operation step of item 804 is completed, the operation step item 804 is indicated as completed with the hatching. Further, operation steps of items 814 and 815, which are sequential of operation step of item 804, are now selectable which is indicated on the display screen 800 accordingly. Still further, the operation step item 806 is now no longer selectable since this operation step may interfere with the function of the apparatus in the current state.

In the above illustrations, for the sake of easier understanding, several non-selectable operation step items are displayed. However, e.g. for the sake of screen area economy or easier overview, the displaying of such operation step items may be omitted. For example in FIG. 11 when the "Service" operation item 806 is no longer selectable, the displaying of this item may be omitted to leave room for the other operation step items or for any other item, such as an indicator, progress bar, information item, etc.

In FIG. 11, the operator may select if the "Prime" operation step 814 or the "Prescription" operation step 815 should be performed next since there is no dependency between these operation steps. The "Disinfection" operation step 805 is also selectable since it does not interfere with the present state of the dialysis procedure. In the description below, it is assumed that the user selects the priming operation step before the prescription operation step such that the priming may proceed while the prescription step is taken care of. However, the opposite order is equally possible in this example. Further, for the sake of time saving, the priming operation step 814 may here be indicated as recommended next operation step, although any of the priming operation step 814 and the prescription operation step 815 are selectable.

Figure 12:
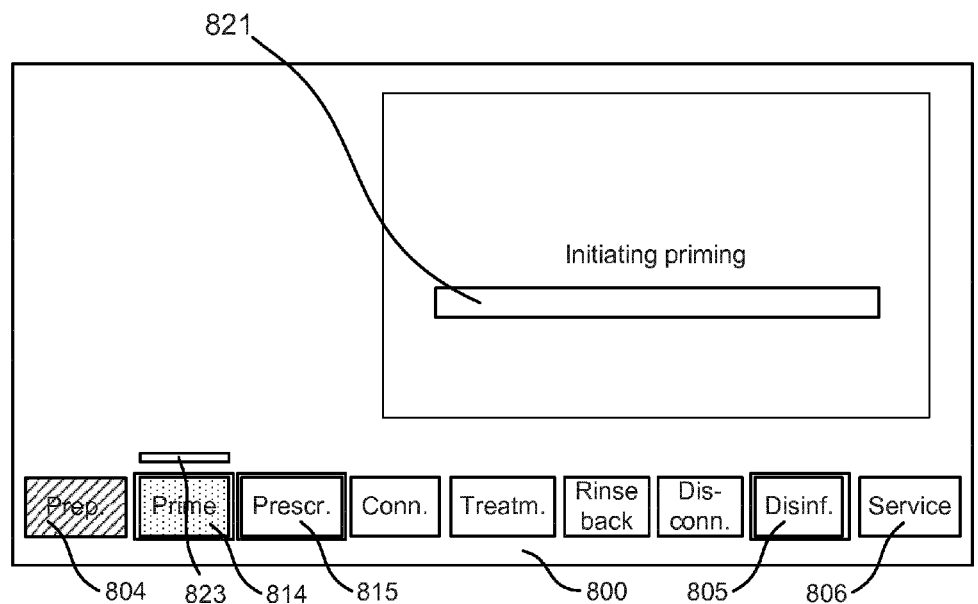
Figure 13:
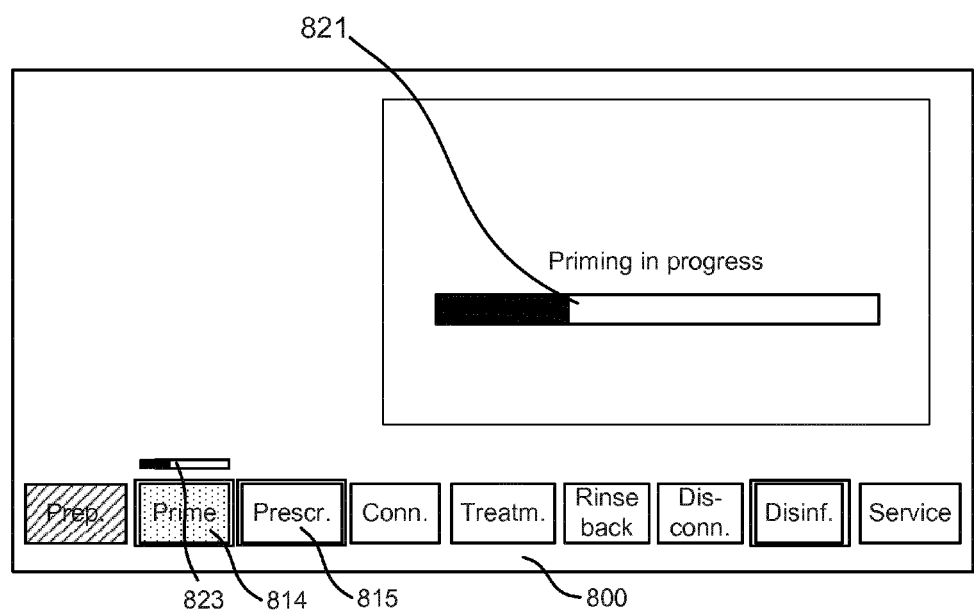

FIG. 12 illustrates a snap shot of the display screen 800 of the UI at a later time instant than that for FIG. 11, where operation step item 814 is interacted with and information is provided that priming is initiated. Here it may be noted that operation step item 806 is not selectable for similar reasons as demonstrated above, while the same operation steps that were available in FIG. 11 are still available. FIG. 13 illustrates a corresponding screen at a later instant where a progress bar 821 may be displayed indicating the progress of priming. A miniature 823 of the progress bar 821 may also be provided in connection with the operation step item 814.

Figure 14:
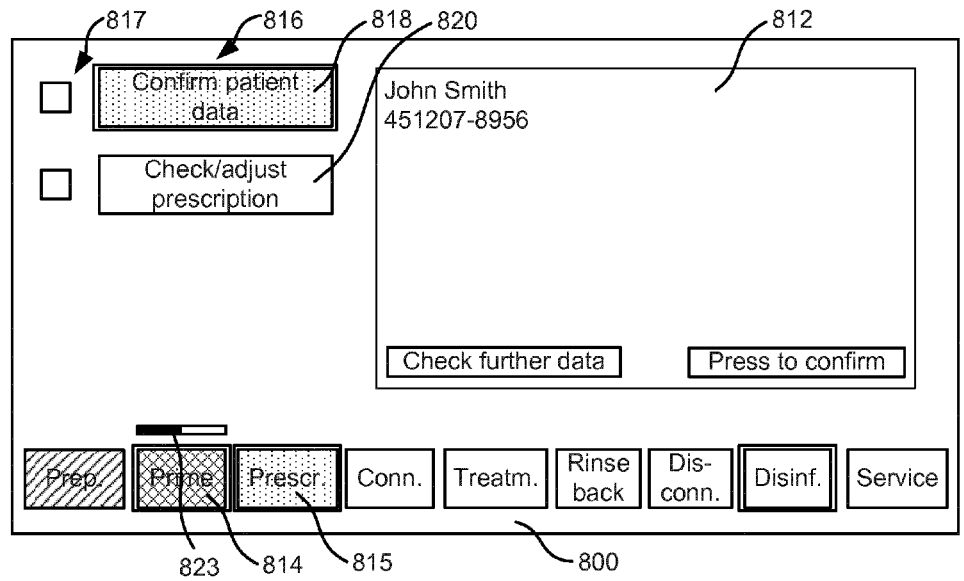

FIG. 14 illustrates a snap shot of the display screen 800 of the UI at a later time instant than that for FIG. 13, where operation step item 815 is interacted with, and a number of operation substep items 816 are displayed, also here with optional check box or status indicators 817. Operation substep item 818 is activated, by the operator through interaction or by the UI controller as a suggested next action, and corresponding information and/or input prompts are displayed in the guided interaction field area 812. It should be noted that operation step item 814 may be indicated as being in progress, here indicated with a fishnet area of the operation step item 814. Further, a progress bar may be provided in connection with the operation step item 814.

Figure 15:
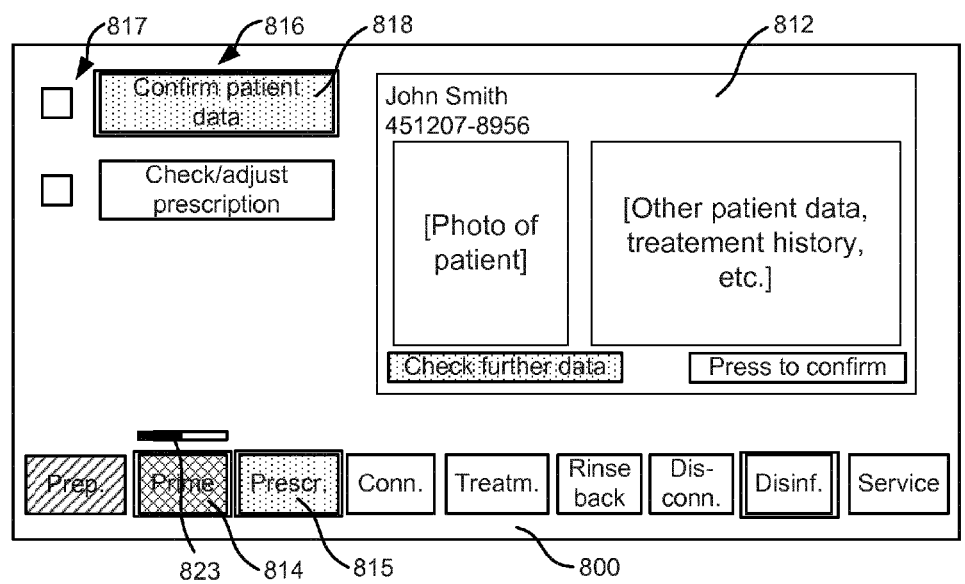
Figure 16:
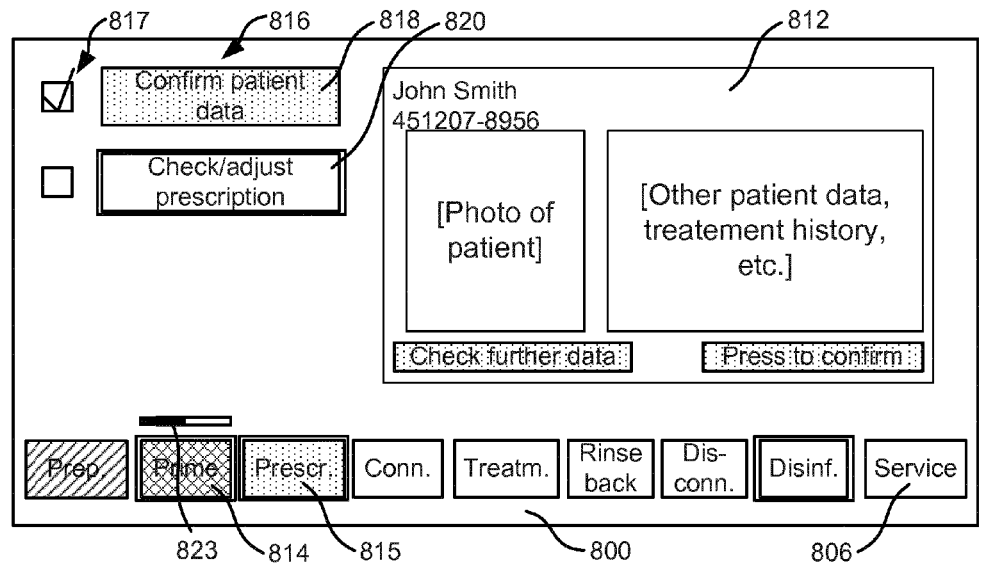
Figure 17:
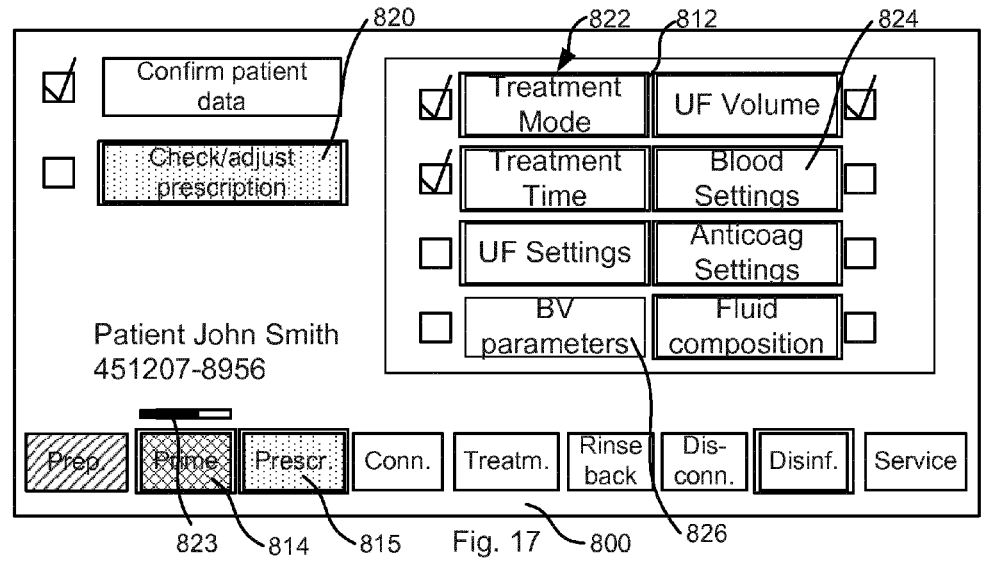
Figure 18:
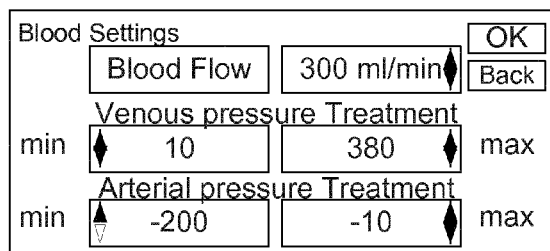
Figure 19:
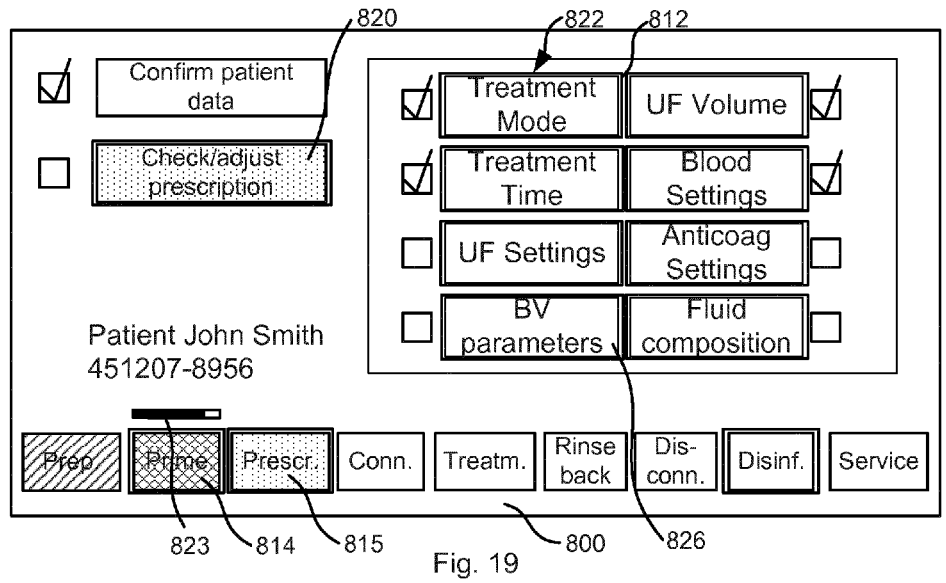

Here, operation substep item 820 is not selectable since it is sequential in relation to or depending on confirmation of patient data operation substep item 818. The patient data may be presented in the guided interaction field 812, and optionally may soft buttons be provided for checking details and/or confirming be provided in the guided interaction field 812. FIG. 15 illustrates that the user has pressed the "Check further data" button in the guided interaction field, wherein further information about the patient is presented in the guided interaction field, and the user may confirm if the patient data is correct. Upon such confirmation, as illustrated in FIG. 16 which illustrates a snap shot of the display screen 800 of the UI at a later time instant than that for FIG. 15, the operation substep of item 818 is indicated as completed and operation substep item 820 may be activated. FIG. 17 illustrates that operation substep item 820 is selected. Similar to what is demonstrated for substep item 818, the selection may be activated by the operator through interaction or by the UI controller as a suggested next action. A number of items 822 of further detail corresponding to operation substep of item 820 are displayed, e.g. in the guided interaction field area 812. Here, in the snap shot of the display screen 800 of the UI, some of the items of further detail are completed which is indicated. At least some of the items 822 of further detail may be activated to for example view a parameter setting view, as illustrated in FIG. 18 which corresponds to activation of the item 824 of further detail, e.g. in the guided interaction field area 812. Other views may be guidance, such as text, images and/or animations, which are viewed upon interaction of an item of further detail. Further, operation substep of further detail 826 related to blood volume (BV) parameters is indicated as non-selectable since this requires that a blood volume sensor (BVS) is installed. Upon any interaction by the operator with the non-selectable item 826, the UI may provide an instruction view telling the operator that this substep is only available upon installation of the BVS, and optionally/ selectably may also information about installation be provided. Sensors of the apparatus monitors whether a BVS is installed, and upon sensor input that the BVS is installed, BV parameters may be set, as illustrated in FIG. 19. Corresponding sensor dependencies may be present for other operation steps, operation substeps, etc.

Figure 20:
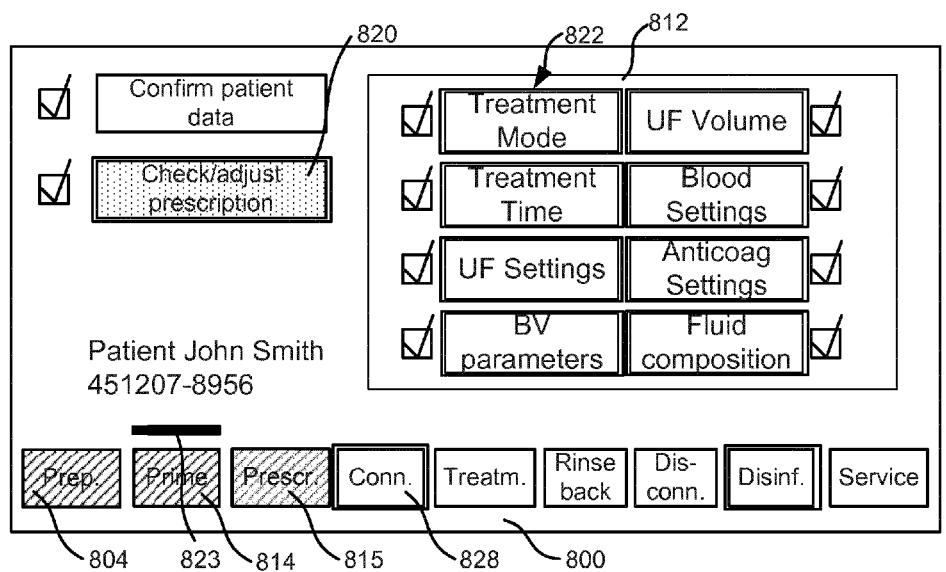
Figure 21:
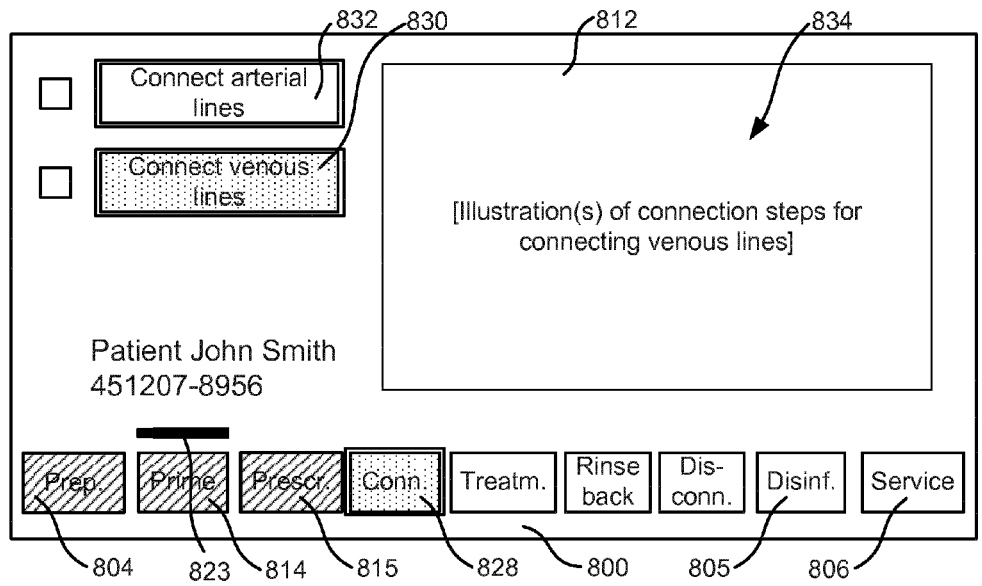

FIG. 20 illustrates a snap shot of the display screen 800 of the UI at a later time instant than that for FIG. 19, where the operation substeps of items 818 and 820 are completed and operation step item 828 becomes selectable. Upon selection of operation step item 828, as illustrated in FIG. 21, guidance and/or substeps, etc., are provided corresponding to the principles that have been demonstrated above. In FIG. 21, both operation substep items 830 and 832 are selectable, and the user has here selected operation substep item 830, wherein illustrative guidance 834 is provided in the guided interaction field 812. Here it may be noted that operation step item 805 is not selectable for similar reasons as demonstrated above. The operation step items 804, 814 and 815 indicate their corresponding operation steps as completed. Here, all the completed operation step items are displayed, but that is not necessary. For the same reasons as demonstrated above for non-selectable operation step items, the displaying of one or more of the completed operation step items may be omitted due to screen area economy and/or overview considerations. It is also preferable that completed operation step items may be interacted with, although not selected, to enable view of performed actions, states or settings. This may for example be of interest when shifting user during the process, e.g. from night shift to day shift.

By the approach demonstrated by the example screen snap shots of FIGS. 8 to 21, a very detailed guidance through the process for dialysis may be provided. This detailed guidance may be mandatory for safeguarding the proper handling through the process. It may also be optional. One example is that the most detailed guidance is mandatory for a user that is not particularly trained for the particular process, e.g. a patient doing home dialysis, or a nurse at a trauma centre (being very skilled in other medical issues, but less in dialysis procedures). There may be different levels of guidance, as can be understood from the demonstration above of operation steps, operation substeps, operation steps of further detail and setting and guidance on a still further level of detail. A particularly trained user, such as a nurse at a dialysis centre, may for example only have the operation steps as mandatory, on which an example will be given with reference to FIGS. 22 to 25. However, for such a particularly trained user, the option to get further guidance, as of e.g. FIGS. 8 to 21, can also be beneficial in some situations, e.g. after returning from a long vacation.

Figure 22:
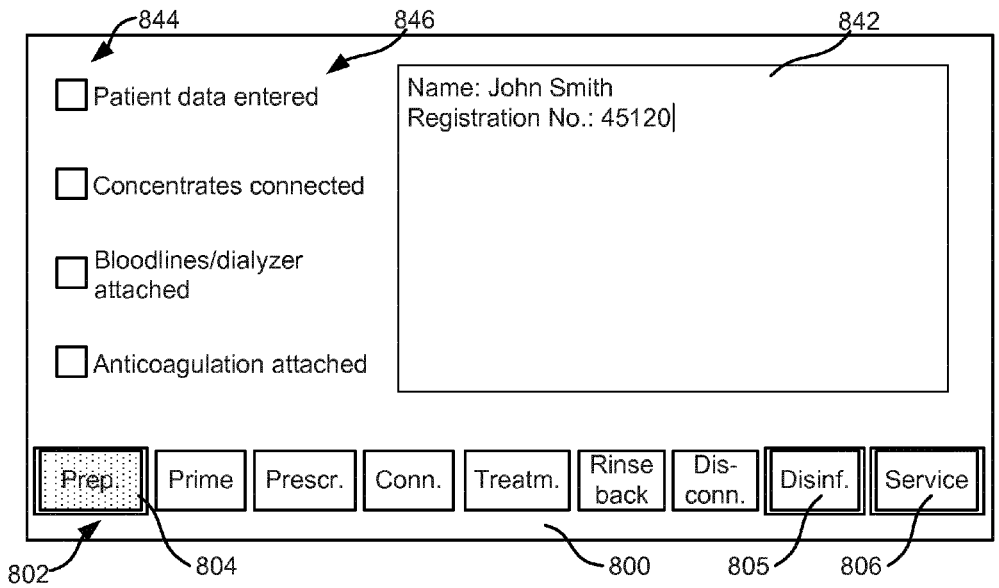
FIGS. 22 to 25 illustrate a user interface example according to a second user interface setting.

FIG. 22 illustrates a snap shot of a display screen 800 of a UI according to an embodiment. The type of touch display and way of indicating operation step items 802 is similar to what is demonstrated with reference to FIGS. 8 to 21 for easier comparison of the approaches, and the work area that in the examples demonstrated with reference to FIGS. 8 to 21 was a guided interaction field is here an input field 842. Here, a check field with check boxes 844 and issue descriptors 846 may be provided for the respective operation step items 802 upon selection. The check boxes 844 are checked by the user and/or when sensor signals indicates that the respective issue is solved/performed. Thus, the trained user can perform the steps with minimized interaction with the user interface. In FIG. 22, the preparation operation step item 804 is selected, wherein the issue descriptors 846 and their check boxes are displayed. The input field 842 displays a form for manual entry of patient data. The user can thus type the patient data, but if for example an electronic patient card or patient data server is read, the patient data is automatically entered and the check box for entering patient data becomes ticked. The other check boxes are preferably ticked based on sensor signals of sensors monitoring connections and attachments. The user can also tick the boxes manually upon performed actions.

For the easier understanding, the operation steps, substeps, substeps of further detail and items of still further detail, etc. has been explained as if all being mandatory, but that is not necessarily the case. As is understood from the disclosure above, the service operation step is not mandatory for the dialysis, but this may also apply for some substeps, substeps of further detail and items of still further detail, etc. In some embodiments, such exclusively optional operation steps, substeps, substeps of further detail and items of still further detail, etc. may be indicated as such by the corresponding displayed items.

Figure 23:
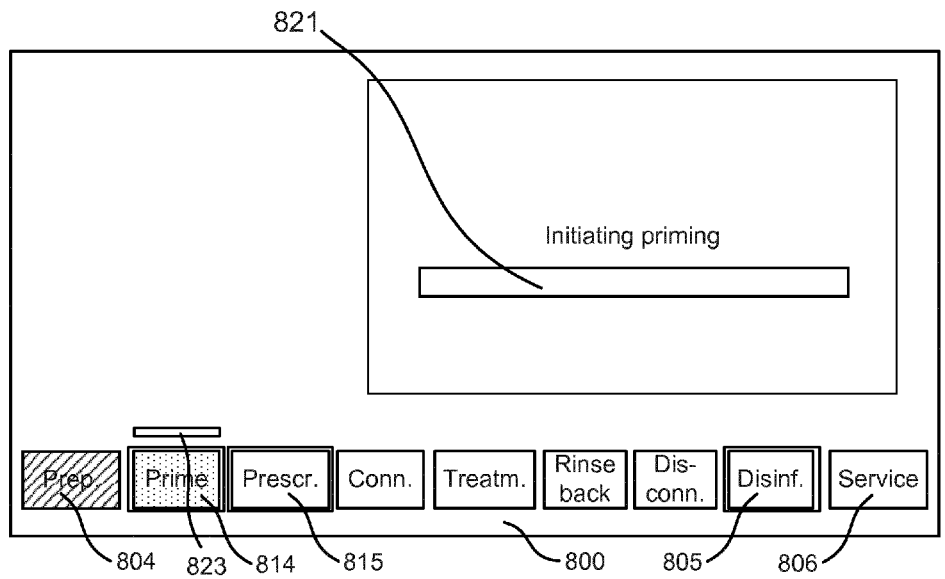

FIG. 23 illustrates a snap shot of the display screen 800 of the UI at a later time instant than that for FIG. 22, where the operation step of item 804 is completed and operation items 814 and 815 become selectable. The user has here selected the priming operation step item 814 and the priming is initiating. Consequently, the service operation step item 806, as demonstrated above, is no longer selectable.

Figure 24:
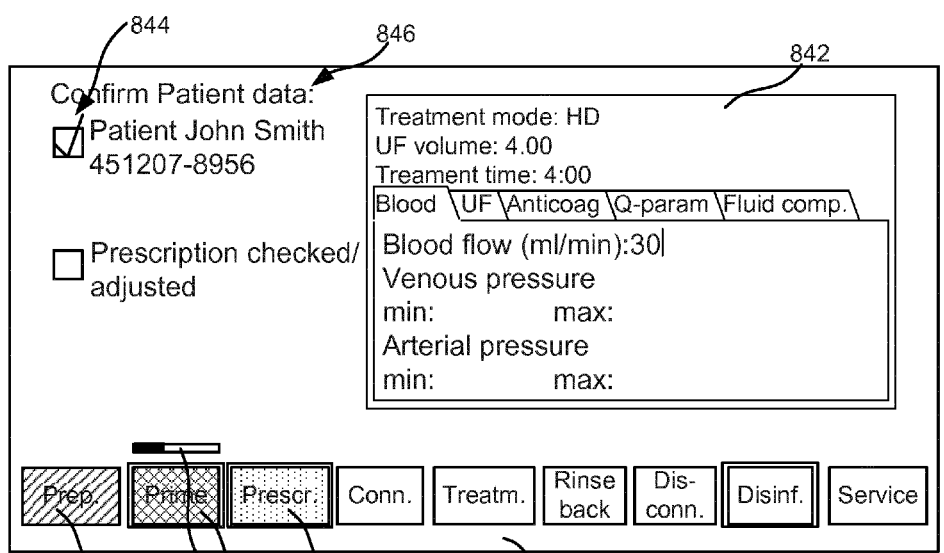

FIG. 24 illustrates a snap shot of the display screen 800 of the UI at a later time instant than that for FIG. 23, where the operation step of item 804 is indicated as completed and operation item 814 is indicated as in progress. The user has here selected operation step item 815, and an input form for prescription parameters is displayed in the input field 842. Check boxes and issue descriptors are also displayed and the user can tick the check boxes to confirm patient data, as performed in FIG. 24, and the prescription parameters.

Figure 25:
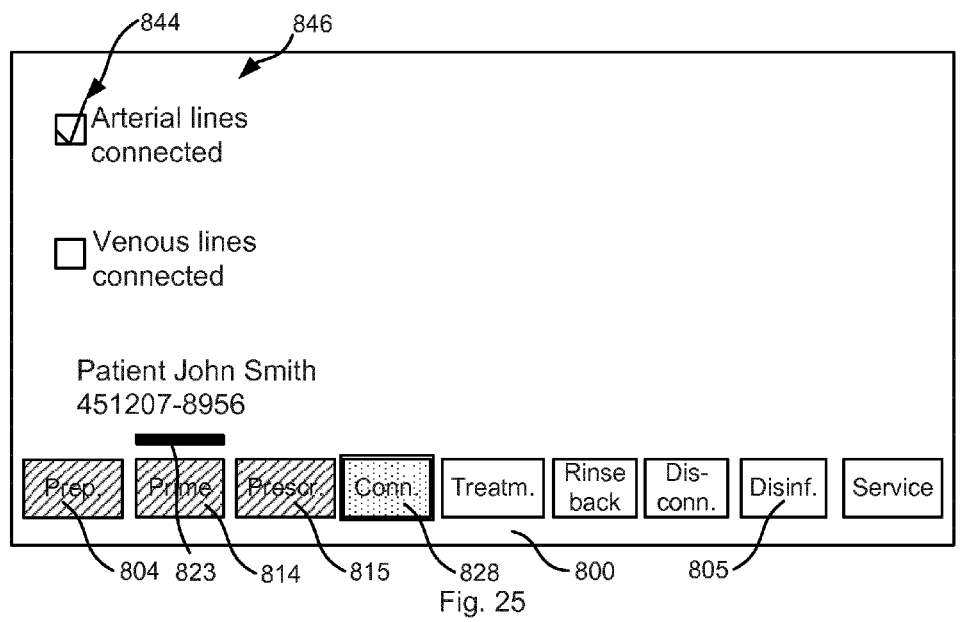

FIG. 25 illustrates a snap shot of the display screen 800 of the UI at a later time instant than that for FIG. 24, where the operation steps of items 804, 814 and 815 are completed and operation step item 828 is selected. The user ticks off the check boxes as the actions are performed, and the procedure continues according to the here demonstrated principles. Here it can be noted that operation step item 806 is not selectable for similar reasons as demonstrated above.

The examples given with reference to FIGS. 8 to 25 give an illustrative view on how the principles may be applied for examples of dialysis processes and dialysis apparatuses. The reader skilled in the field of technology readily understands that the operation steps of the examples may be others than those mentioned, and the operation step items may look different from those depicted. A more abstract demonstration of the principles will now be given below and with reference to tables 1 to 4. Also here does the skilled reader understand that the number of operation steps, their interrelations, etc. may be other than those explicitly given by the tables.

In a first example, the initial states for a set of operation steps are assumed to be determined according to the principles demonstrated above at a first time instance t=0. The conditions may then be like given in Table 1. Here it may be seen that the "state" associated with an operation item may be a set of state parameters, such as dependence state, completion state and selectability state. According to an embodiment, implementation of management of the operation step items (and substep items) may include forming a data structure resembling the structure demonstrated by the tables.

TABLE 1

First state table at a first time instant t = 0.

| Time | Operation step | Dependence | Operation step item (GUI item) | Completion state | Selectability state |
|---|---|---|---|---|---|
| t = 0 | 1 | Non-sequential | A | Non-completed | Selectable |
|  | 2 | Sequential | B | Non-completed | Selectable |
|  | 3 | Non-sequential | C | Non-completed | Selectable |
|  | 4 | Sequential | D | Non-completed | Non-selectable |
|  | 5 | Non-sequential | E | Non-completed | Selectable |

At a second time instant t=1, later than t=0, where interaction with operation step item A may have been performed by selection by the operator, and operation steps 1 and 2 have been completed, the conditions may be like given in Table 2. For convenience, differences to Table 1 is given in italics.

TABLE 2

Second state table at a second time instant t = 1.

| Time | Operation step | Dependence | Operation step item (GUI item) | Completion state | Selectability state |
|---|---|---|---|---|---|
| t = 1 | 1 | Non-sequential | A | *Completed* | *Non-selectable* |
|  | 2 | Sequential | B | *Completed* | *Non-selectable* |
|  | 3 | Non-sequential | C | Non-completed | Selectable |
|  | 4 | Sequential | D | Non-completed | *Selectable* |
|  | 5 | Non-sequential | E | Non-completed | Selectable |

Assume that interaction is performed with operation step item E rendering in completing operation step 5. The conditions will then be like given in Table 3.

TABLE 3

Third state table at a second time instant t = 2.

| Time | Operation step | Dependence | Operation step item (GUI item) | Completion state | Selectability state |
|---|---|---|---|---|---|
| t = 2 | 1 | Non-sequential | A | Completed | Non-selectable |
|  | 2 | Sequential | B | Completed | Non-selectable |
|  | 3 | Non-sequential | C | Non-completed | Selectable |
|  | 4 | Sequential | D | Non-completed | Selectable |
|  | 5 | Non-sequential | E | *Completed* | *Non-selectable* |

In a second example, initial states have been determined, similar to as assumed above, and the operator is enabled to perform selectable operation steps in desired order. The conditions is thus as given in Table 1. However, in this example, performing one operation step causes removal of another operation step and a new operation step is introduced as a causality. The change may also cause in a change of order in the structure of the steps. For example, the operator connects another type of blood line set than assumed for generating Table 1. Here it is assumed that the connection of the another type of blood line set is not made by error, which would cause an alarm event and which is not the subject of this disclosure, and the another type of blood line set just changes the dialysis procedure to another variant. Therefore, the UI is updated with a new set of operation step items A' to E'. The state parameter of dependence can here be seen to be slightly different since operation step 3' is sequential (operation step 3 was non-sequential), which renders operation step item C' non-selectable. The conditions is thus as given by Table 4.

TABLE 4

Second state table at a second time instant t = 1.

| Time | Operation step | Dependence | Operation step item (GUI item) | Completion state | Selectability state |
|---|---|---|---|---|---|
| t = 1 | 1' | Non-sequential | A' | Non-completed | Selectable |
|  | 2' | Sequential | B' | Non-completed | Selectable |
|  | 3' | *Sequential* | C' | Non-completed | *Non-selectable* |
|  | 4' | Sequential | D' | Non-completed | Non-selectable |
|  | 5' | Non-sequential | E' | Non-completed | Selectable |

Numerous of similar examples can be given where the principles of adapting the UI to the dialysis process, and by the further adapting to the preferences or skills of the operator provides a versatile, secure and efficient UI support for the operator of an apparatus for dialysis process.

As can be readily recognised when comparing the approach demonstrated with reference to FIGS. 8 to 21 and the approach demonstrated with reference 22 to 25, the approach of FIGS. 22 to 25 requires that the user knows the actions to be made, but the process can be progressed with much less interaction with the UI. The particularly trained user can thus make progress in the process in a way that may be experienced smother and faster. If the particularly trained user anyway wants to get more guidance or use any of the input screens as of any of FIGS. 8 to 22, that may be called upon through the user interface. The versatility for the particularly trained user is thus enhanced. The levels of detail, e.g. presentation of operation step items, operation substep items, items of further detail and items of still further detail, etc. can thus be considered as an information zoom tool where more or less detailed guidance and/or guided input screens may be provided.

The invention has mainly been described above with reference to a few embodiments. However, as is readily appreciated by a person skilled in the art, other embodiments than the ones disclosed above are equally possible within the scope of the invention, as defined by the appended patent claims.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and the scope of the appended claims.

The invention claimed is:

1. An apparatus for performing a plurality of operation steps of a dialysis process, said apparatus comprising:
a process controller for controlling the apparatus to perform the operation steps of the dialysis process, monitor process progress of the dialysis process and monitor sensor inputs of sensors of the apparatus; and
a user interface comprising a display, an input device and a user interface controller, wherein the user interface controller is connected to enable presentation of graphical data on the display, and wherein the user interface controller is connected to enable user interaction with the graphical data and connected to exchange information with the process controller, wherein the exchanged information is based on the user interaction of the user interface and monitoring of process progress of the dialysis process and sensor inputs of sensors of the apparatus monitored by the process controller, and wherein
each of the operation steps are classified in the user interface controller as one of a sequential operation step, which is dependent on completion of another operation step, and a non-sequential operation step, which is independent of completion of another operation step,
the user interface controller is configured to represent each of the operation steps by an operation step item which is a graphical item suitable to be presented on said display, and
the user interface controller is further configured to dynamically, for each of the operation steps, control enabling and disabling of selection among the corresponding operation step items based on a state of the respective operation step, wherein a completed state is assigned to each operation step that is completed, a non-completed state is assigned to each operation step that is non-completed, a selectable state is assigned to each operation step item of an operation step that is non-sequential and each operation step item of an operation step that is sequential but only in relation to a completed operation step, and a non-selectable state is assigned to each operation step item of an operation step that is sequential in relation to a non-completed operation step.

2. The apparatus according to claim 1, wherein the user interface controller is arranged to dynamically classify the operation steps during the dialysis process as sequential or non-sequential based on any of process progress, sensor input and input parameter settings.

3. The apparatus according to claim 2, wherein the process controller or user interface controller is arranged to cause display of the operation steps based on any of status of peripherals or consumables used by the apparatus during the dialysis process.

4. The apparatus according to claim 1, wherein the process controller or user interface controller is arranged to dynamically during the dialysis process add or remove an operation step item from the display based on any of process progress and input parameter settings.

5. The apparatus according to claim 1, wherein the amount of operation guidance information of an operation step item is selectable by the operator.

6. The apparatus according to claim 1, wherein one or more operation step items of said operation step items assigned a selectable state recommended to be performed next are displayed with an indicator representing the recommendation.

7. The apparatus according to claim 1, wherein all operation step items representing an operation step with a process in progress by the process controller are displayed with a status indicator representing the progress.

8. The apparatus according to claim 1, wherein at least one of the operation step items comprises operation substep items that represent substeps of the at least one operation step by at least one of operation guidance, parameter setting and status information, and wherein the user interface controller is arranged to enable displaying of the operation substep items upon displaying of the corresponding operation step item.

9. The apparatus according to claim 8, wherein the user interface controller is arranged to enable the displaying of the operation substep items upon displaying of the corresponding operation step item based on an input from the operator, wherein such enabling based on input from the operator overrides any corresponding disabling of the displaying of the operation substep items by the user interface controller.

10. The apparatus according to claim 8, wherein the user interface controller is arranged to disable the displaying of the operation substep items upon displaying of the corresponding operation step item based on an input from the operator.

11. The apparatus according to claim 8, wherein the user interface controller is arranged to disable the displaying of the operation substep items upon displaying of the corresponding operation step item based on a determined skill level of the operator.

12. The apparatus according to claim 8, wherein at least one of the operation substep items comprises operation substep items on a further level of detail that represent operation substeps on a further level of detail of the at least one substep by at least one of operation guidance, parameter setting and status information, and wherein the user interface controller is arranged to enable displaying of the operation substep items on a further level of detail upon displaying of the corresponding operation substep item.

13. The apparatus according to claim 12, wherein the user interface controller is arranged to enable the displaying of the operation substep items on a further level of detail upon displaying of the corresponding operation substep item based on an input from the operator, wherein such enabling based on input from the operator overrides any corresponding disabling of the displaying of the operation substep items on a further level of detail by the user interface controller.

14. The apparatus according to claim 12, wherein the user interface controller is arranged to disable the displaying of the operation substep items on a further level of detail upon displaying of the corresponding operation substep item based on an input from the operator.

15. The apparatus according to claim 12, wherein the user interface controller is arranged to disable the displaying of the operation substep items on a further level of detail upon displaying of the corresponding operation substep item based on a determined skill level of the operator.

16. The apparatus according to claim 1, wherein the user interface controller is arranged to enable displaying of all of said operation step items assigned a selectable state through said user interface.

17. The apparatus according to claim 1, wherein the user interface controller is arranged to enable displaying of only a subset of said operation step items assigned a selectable state through said user interface.

18. The apparatus according to claim 1, wherein an operation step is assigned a completed state by any of user interaction through said user input device, a signal from said process controller, and a sensor signal from a sensor of the apparatus, or any combination thereof.

19. The apparatus according to claim 1, wherein the user interface controller, based on said assignment, is arranged to enable one or more of said operation step items assigned a non-selectable state to be displayed through said user interface.

20. The apparatus according to claim 1, wherein one or more operation step items of completed operation steps are displayed with a status indicator representing the completion.

21. The apparatus according to claim 20, wherein all operation step items of completed operation steps are displayed.

22. The apparatus according to claim 20, wherein all operation step items of completed operation steps on which a sequential operation step relies upon are displayed.

23. A computer program comprising computer-executable program code which when executed by a processor of an apparatus for a dialysis process having a process controller and a user interface including a display, an input device and a user interface controller, causes the apparatus to:
perform a plurality of operation steps of the dialysis process, monitor process progress of the dialysis process and monitor sensor inputs of sensors of the apparatus;
classify each of the operation steps as one of a sequential operation step, which is dependent on completion of another operation step, and a non-sequential operation step, which is independent of completion of another operation step,
display each of the operation steps by an operation step item which is a graphical item suitable to be presented on said display; and
dynamically, for each of the operation steps, enable and disable selection among the corresponding operation step items based on a state of the respective operation step, wherein a completed state is assigned to each operation step that is completed, a non-completed state is assigned to each operation step that is non-completed, a selectable state is assigned to each operation step item of an operation step that is non-sequential and each operation step item of an operation step that is sequential but only in relation to a completed operation step, and a non-selectable state is assigned to each operation step item of an operation step that is sequential in relation to a non-completed operation step.

* * * * *